US010176408B2

(12) United States Patent
Paik et al.

(10) Patent No.: US 10,176,408 B2
(45) Date of Patent: Jan. 8, 2019

(54) SYSTEMS AND METHODS FOR ANALYZING PATHOLOGIES UTILIZING QUANTITATIVE IMAGING

(71) Applicants: David S. Paik, Half Moon Bay, CA (US); Andrew J. Buckler, Wenham, MA (US); Kjell Johnson, Ann Arbor, MI (US); Xiaonan Ma, South Hamilton, MA (US); Keith A. Moulton, Amesbury, MA (US)

(72) Inventors: David S. Paik, Half Moon Bay, CA (US); Andrew J. Buckler, Wenham, MA (US); Kjell Johnson, Ann Arbor, MI (US); Xiaonan Ma, South Hamilton, MA (US); Keith A. Moulton, Amesbury, MA (US)

(73) Assignee: Elucid Bioimaging Inc., Wenham, MA (US)

( * ) Notice: Subject to any disclaimer, the term of this patent is extended or adjusted under 35 U.S.C. 154(b) by 102 days.

(21) Appl. No.: 14/959,732

(22) Filed: Dec. 4, 2015

(65) Prior Publication Data

US 2017/0046839 A1 Feb. 16, 2017

Related U.S. Application Data

(60) Provisional application No. 62/205,295, filed on Aug. 14, 2015, provisional application No. 62/205,305,
(Continued)

(51) Int. Cl.
*G06K 9/00* (2006.01)
*G06K 9/62* (2006.01)

(52) U.S. Cl.
CPC ....... *G06K 9/6296* (2013.01); *G06K 9/00147* (2013.01)

(58) Field of Classification Search
CPC ............... G06K 9/6296; G06K 9/6278; G06K 9/00147; G06K 9/46
(Continued)

(56) References Cited

U.S. PATENT DOCUMENTS

| | | | | |
|---|---|---|---|---|
| 6,108,635 | A | 8/2000 | Herren et al. | |
| 2005/0043614 | A1 * | 2/2005 | Huizenga ............... | A61B 5/055 600/427 |

(Continued)

FOREIGN PATENT DOCUMENTS

| | | | | |
|---|---|---|---|---|
| WO | 2015058151 A2 | 4/2015 | | |
| WO | WO 2015058151 A2 * | 4/2015 | ......... | A61K 51/0478 |

OTHER PUBLICATIONS

Castellano et al. "Texture analysis of medical images," Clinical Radiology, Dec. 1, 2004 (Dec. 1, 2004) vol. 59.*

(Continued)

*Primary Examiner* — Van D Huynh
(74) *Attorney, Agent, or Firm* — Burns & Levinson, LLP; Gabriel Goldman, Esq.

(57) ABSTRACT

Systems and methods for analyzing pathologies utilizing quantitative imaging are presented herein. Advantageously, the systems and methods of the present disclosure utilize a hierarchical analytics framework that identifies and quantify biological properties/analytes from imaging data and then identifies and characterizes one or more pathologies based on the quantified biological properties/analytes. This hierarchical approach of using imaging to examine underlying biology as an intermediary to assessing pathology provides many analytic and processing advantages over systems and methods that are configured to directly determine and characterize pathology from underlying imaging data.

70 Claims, 10 Drawing Sheets

Related U.S. Application Data filed on Aug. 14, 2015, provisional application No. 62/205,313, filed on Aug. 14, 2015, provisional application No. 62/205,322, filed on Aug. 14, 2015, provisional application No. 62/219,860, filed on Sep. 17, 2015.

(58) Field of Classification Search
USPC .......................................................... 382/131
See application file for complete search history.

(56) References Cited

U.S. PATENT DOCUMENTS

| | | | | |
|---|---|---|---|---|
| 2007/0130206 | A1 | 6/2007 | Zhou et al. | |
| 2009/0171871 | A1 | 7/2009 | Zhang et al. | |
| 2009/0324126 | A1* | 12/2009 | Zitnick | G06T 5/003 382/275 |
| 2010/0070448 | A1 | 3/2010 | Omoigui | |
| 2011/0026798 | A1* | 2/2011 | Madabhushi | G01R 33/56 382/131 |
| 2012/0278060 | A1* | 11/2012 | Cancedda | G06F 17/2818 704/2 |
| 2015/0154275 | A1 | 6/2015 | Senart et al. | |
| 2016/0314580 | A1* | 10/2016 | Lloyd | G06K 9/0014 |
| 2017/0358079 | A1* | 12/2017 | Gillies | A61B 6/469 |

OTHER PUBLICATIONS

Choi et al. "Multiscale image segmentation using wavelet-domain hidden Markov models" IEEE Trans Image Process, Sep. 1, 2001 (Sep. 1, 2001), vol. 10.*

Reddy et al. "Confidence guided enhancing brain tumor segmentation in multi-parametric MRI" Proceedings of the 12th International Conference on Medical Image Computing and Computer-Assisted Intervention, MICCAI 2009, held in London, UK, Sep. 20, 2009.*

Khan et al., "Robust atlas-based brain segmentation using multi-structure confidence-weighted registration" Proceedings of the 12th International Conference on Medical Image Computing, Sep. 20, 2009.*

International Search Report & Written Opinion in co-pending International patent Application No. PCT/US2016/065132 dated Mar. 17, 2017. (17 Pages).

Reedy et al. "Confidence guided enhancing brain tumor segmentation in multi-parametric MRI" Proceedings of the 12th International Conference on Medical Image Computing and Computer-Assisted Intervention, MICCAI 2009, held in London, UK, Sep. 20, 2009.

Kahn et al., "Robust atlas-based brain segmentation using multi-structure condence-weighted registration" Proceedings of the 12th International Conference on Medical Image Computing, Sep. 20, 2009.

Ariff et al. "Carotid Artery Hemodynamics: Observing Patient-specific Changes with Amlodipine and Lisinopril by Using MRI Imaging Computation Fluid Dynamics." Radiol. 257.3(2010):662-669.

Bourque et al. "Usefulness of Cardiovascular Magnetic Resonance Imaging of the Superficial Femoral Artery for Screening Patients with Diabetes Mellitus for Artherosclerosis." Am. J. Cardiol. 110. 1(2012):50-56.

Buckler et al. "A Collaborative Enterprise for Multi-Stakeholder Participation in the Advancement of Quantitative Imaging." Radiol. 258.3(2011):906-914.

Buckler et al. "Data Sets for the Qualification of CT as a Quantitative Imaging Biomarker in Lung Cancer." Optics Exp. 18.14(2010):16.

Buckler et al. "Data Sets for the Qualification of Volumetric CT as a Quantitative Imaging Biomarker in Lung Cancer." Optics Exp. 18.14(2010):15267-15282.

Buckler et al. "Quantitative Imaging Test Approval and Biomarker Qualification: Interrelated but Distinct Activities." Radiol. 259. 3(2011):875-884.

Buckler et al. "Standardization of Quantitative Imaging: The Time is Right and 18F-FDG PET/CT is a Good Place to Start." J. Nuclear Med. 52.2(2011):171-172.

Buckler et al. "The Use of Volumetric CT as an Imaging Biomarker in Lung Cancer." Acadmic Radiol. 17.1 (2010):100-106.

Buckler et al. "Volumetric CT in Lung Cancer: An Example for the Qualification of Imaging as a Biomarker." Academic Radiol. 17.1(2010):107-115.

Buyse et al. "The Validation of Surrogate Endpoints in Meta-Analysis of Randomized Experiments." Biostat. 1 (2000):1-19.

Chan et al. "Active Contours without Edges." IEEE Trans. Image Process. 10.2(2001):266-277.

de Weert et al. "In Vivo Characterization and Quantification of Atherosclerotic Carotid Plaque Components with Multidetector Computed Tomography and Histopathological Correlation." Arterioscler. Thromb. Vasc. Biol. 26.10 (2006):2366-2372.

Fleming. "Surrogate Endpoints and FDA's Accelerated Approval Process." Health Affairs. 24.1(2005):67-78.

Freedman et al. "Statistical Validation of Intermediate Endpoints for Chronic Diseases." Stat. Med. 11(1992):167-178.

Fuleihan et al. "Reproducibility of DXA Absorptiometry: A Model for Bone Loss Estimates." J. Bone Miner. Res. 10.74 (1995):1004-1014.

Horie et al. "Assessment of Carotid Plaque Stability Based on Dynamic Enhancement Pattern in Plaque Components with Multidetector CT Angiography." Stroke. 43.2(2012):393-398.

Irace et al. "Human Common Carotid Wall Shear Stress as a Function of Age and Gender: A 12-year Follow-up Study." AGE. 34.6(2012):1553-1562.

Jaffe, "Measures of Response: RECIST, WHO, and New Alternatives." J. Clin. Oncol. 24.20(2006):3245-3251.

Katz, "Biomarkers and Surrogate Markers: An FDA Perspective." NeuroRx. 12(2004):189-195.

Kerwin et al. "MRI of Carotid Artherosclerosis." Am. J. Roentgenol. 200.3(2013):W304-W313.

Kim et al. "A Curve Evolution-based variational approach to Simultaneous Image Restoration and Segmentation." IEEE Int. Conf. Image Proc. (2002):1-109.

Lathia et al. "The Value, Qualification, and Regulatory Use of Surrogate End Points in Drug Development." Clin. Pharmacol. Therapeutics. 86.1(2009):32-43.

Mozley et al. "Change in Lung Tumor Volume as a Biomarker of Treatment Response: A Critical Review of the Evidence." Ann. Oncol. 21.9(2010):1751-1755.

Phinikaridou et al. "Regions of Low Endothelial Shear Stress Colocalize with Positive Vascular Remodeling and Atherosclerotic Plaque Disruption: An in vivo Magnetic Resonance Imaging Study." Circ. Cardiovasc. Imaging. 6.2 (2013):302-310.

Prentice, "Surrogate Endpoints in Clinical Trials: Definition and Operational Criteria." Stat. Med. 9(1989):431-440.

Sargent et al. "Validation of Novel Imaging Methodologies for Use as Cancer Clinical Trial End-points." Eur. J. Dis. 45 (2009):290-299.

Sui et al. "Assessment of Wall Shear Stress in the Common Carotid Artery of Healthy Subjects Using 3.0-Tesla Magentic Resonanance." Acta Radiologica. 49.4(2008):442-449.

Ten Kate et al. "Noninvasive Imaging of the Vulnerable Atherosclerotic Plague." Current Problems Cardiol. 35.11 (2010):556-591.

Van Klavern et al. "Management of Lung Nodules Detected by Volume CT Scanning." New Engl. J. Med. 361 (2009):23.

Varma et al. "Coronary Vessel Wall Constrast Enhancement Imaging as a Potential Direct Marker of Coronary Involvement: Integration of Findings from CAD and SLE Patients." JACC Cardiovasc. Imaging. 7.8(2014):762-770.

Wintermark et al. "Carotid Plaque CT Imaging in Stroke and Non-Stroke Patients." Ann. Neurol. 64.2(2008):149-157.

Wintermark et al. "High-Resolution CT Imaging of Carotid Artery Atherosclerotic Plaques." Am. J. Neuroradiol. 29.5 (2008):875-882.

Wong et al. "Imaging in Drug Discovery, Preclinical, and Early Clinical Development." J. Nuclear Med. 49.6 (2008):26N-28N.

Woodcock et al. "The FDA Critical Path Initiative and its Influence on New Drug Development." Annu. Rev. Med. 59 (2008):1-12.

(56) References Cited

OTHER PUBLICATIONS

Zavodni et al. "Carotid Artery Plaque Morphology and Composition in Relation to Incident Cardiovascular Events: The Multi-Ethnic Study of Atherosclerosis (MESA)." Radiol. 271.2(2014):361-389.
Zhao et al. "Evaluating Variability in Tumor Measurements from Same-Day Repeat CT Scans of Patients with Non-Small Cell Lung Cancer." Radiol. 252.1(2009):263-272.

* cited by examiner

Computing Putative Analyte Blobs

SYSTEMS AND METHODS FOR ANALYZING PATHOLOGIES UTILIZING QUANTITATIVE IMAGING

CROSS-REFERENCE TO RELATED APPLICATIONS

The subject application relates and claims priority to U.S. Provisional Application Ser. Nos. 62/205,322, 62/205,313, 62/205,305, 62/205,295 and 62/219,860, the contents of which are incorporated herein in their entirety.

STATEMENT REGARDING FEDERALLY SPONSORED RESEARCH/DEVELOPMENT

This work supported in part by NSF SBIR Award 1248316 and NIH SBIR Award R44 HL126224-01A1 and the government may have certain rights to the work.

BACKGROUND OF THE INVENTION

The present disclosure related to quantitative imaging and analytics. More specifically, the present disclosure relates to systems and methods for analyzing pathologies utilizing quantitative imaging.

Imaging, particularly with safe and non-invasive methods, represents the most powerful methods for locating the disease origin, capturing its detailed pathology, directing therapy, and monitoring progression to health. Imaging is also an extremely valuable and low cost method to mitigate these human and financial costs by allowing for appropriate early interventions that are both less expensive and disruptive.

Enhanced imaging techniques have made medical imaging an essential component of patient care. Imaging is especially valuable because it provides spatially- and temporally-localized anatomic and functional information, using non- or minimally invasive methods. However, techniques to effectively utilize increasing spatial and temporal resolution are needed, both to exploit patterns or signatures in the data not readily assessed with the human eye as well as to manage the large magnitude of data in such a way as to efficiently integrate it into the clinical workflow. Without aid, the clinician has neither the time nor often the ability to effectively extract the information content which is available, and in any case generally interprets the information subjectively and qualitatively. Integrating quantitative imaging for individual patient management as well as clinical trials for therapy development requires a new class of decision support informatics tools to enable the medical community to fully exploit the capabilities of made possible with the evolving and growing imaging modalities within the realities of existing work flows and reimbursement constraints.

Quantitative results from imaging methods have the potential to be used as biomarkers in both routine clinical care and in clinical trials, for example, in accordance with the widely accepted NIH Consensus Conference definition of a biomarker. In clinical practice, quantitative imaging are intended to (a) detect and characterize disease, before, during or after a course of therapy, and (b) predict the course of disease, with or without therapy. In clinical research, imaging biomarkers may be used in defining endpoints of clinical trials.

Quantification builds on imaging physics developments which have resulted in improvements of spatial, temporal, and contrast resolution as well as the ability to excite tissues with multiple energies/sequences, yielding diverse tissue-specific responses. These improvements thereby allow tissue discrimination and functional assessment, and are notably seen, for example, in spectral computed tomography (spectral CT), multi-contrast magnetic resonance imaging (multi-contrast MRI), ultrasound (US), and targeted contrast agent approaches with various imaging modalities. Quantitative imaging measures specific biological characteristics that indicate the effectiveness of one treatment over another, how effective a current treatment is, or what risk a patient is at should they remain untreated. Viewed as a measurement device, a scanner combined with image processing of the formed images has the ability to measure characteristics of tissue based on the physical principles relevant to a given imaging approach and how differing tissues respond to them. Though the image formation process differs widely across modalities, some generalizations help frame the overall assessment, though exceptions, nuances, and subtleties drive the real conclusions and until and unless they are considered some of the greatest opportunities are missed.

Imaging in the early phases of clinical testing of novel therapeutics contributes to the understanding of underlying biological pathways and pharmacological effects. It may also reduce the cost and time needed to develop novel pharmaceuticals and therapeutics. In later phases of development, imaging biomarkers may serve as important endpoints for clinical benefit. In all phases, imaging biomarkers may be used to select or stratify patients based on disease status, in order to better demonstrate therapeutic effect.

SUMMARY

Systems and methods are provided herein which utilize a hierarchical analytics framework to identify and quantify biological properties/analytes from imaging data and then identify and characterize one or more medical conditions based on the quantified biological properties/analytes. In some embodiments, the systems and methods incorporate computerized image analysis and data fusion algorithms with patient clinical chemistry and blood biomarker data to provide a multi-factorial panel that may be used to distinguish between different subtypes of disease. Thus, the systems and methods of the present disclosure may advantageously implement biological and clinical insights in advanced computational models. These models may then interface with sophisticated image processing through rich ontologies that specify technical factors associated with the growing understanding of pathogenesis and takes the form of rigorous definitions of what is being measured and how it is measured and assessed and how it is relates to clinically-relevant subtypes and stages of disease.

Human disease exhibits strong phenotypic differences that can be appreciated by applying sophisticated classifiers on extracted features that capture spatial, temporal, and spectral results measurable by imaging but difficult to appreciate unaided. Traditional Computer-Aided Diagnostics make inferences in a single step from image features. In contrast, the systems and methods of the present disclosure employ a hierarchical inference scheme including intermediary steps of determining spatial image features and time-resolved kinetics at multiple levels of biologically-objective components of morphology, composition and structure which in subsequently are utilized to draw clinical inferences. Advantageously, the hierarchical inference scheme ensures the clinical inferences can be understood, validated, and explained at each level in the hierarchy.

In example embodiments, system and methods are provided which utilize a processor a non-transient storage medium including processor executable instructions implementing an analyzer module including a hierarchical analytics framework configured to (i) utilize a first set of algorithms identify and quantify a set of biological properties utilizing imaging data and (ii) utilize a second set of algorithms to identify and characterize one or more medical conditions based on the quantified biological properties. In some embodiments the analytics framework may implement an algorithm for identifying and characterizing the one or more medical conditions based on the quantified biological properties wherein a training set from one or more non-radiological or non-imaging data sources was used in training the algorithm. In other the analytics framework may implement an algorithm for identifying and quantifying the biological properties utilizing radiological imaging data, wherein a training set from one or more non-radiological data sources was used training the algorithm.

In example embodiments, data from a plurality of same or different types of data sources may be incorporated into the process of identifying and characterizing the one or more medical conditions. In some embodiments, data from one or more non-imaging data sources may be used in conjunction with the imaging data such that the set of biological properties includes one or more biological properties identified or quantified based at least in part on the data from one or more non-imaging data sources. For example, data from non-imaging sources may include one or more of (i) demographics, (ii) results from cultures or other lab tests, (iii) genomic, proteomic or metabolomic expression profiles, or (iv) diagnostic observations. In some embodiments, data from one or more non-radiological data sources may be used in conjunction with radiological imaging data such that the set of biological properties includes one or more biological properties identified or quantified based at least in part on the data from one or more non-radiological data sources.

In example embodiments, information relating to the set of identified and quantified biological properties may be adjusted after an initial identification or quantification thereof based on contextual information which adjusts or updates one or more probabilities impacting the identification or quantification of at least one of the biological properties in the set. For example, the contextual information includes at least one of patient demographics, correlations relating different biological properties, or correlations relating one or more of the identified medical conditions to one or more biological properties. In some embodiments, information relating to the identified and characterized one or more medical conditions may be adjusted after an initial identification or characterization thereof based on contextual information which adjusts or updates one or more probabilities impacting the identification or characterization of at least one of one or more medical conditions.

In example embodiments, the systems and methods of the present disclosure may be configured to provide a user with information relating both the one or more medical conditions as well as relating to the underlying biological properties used in the identification or characterization of the one or more medical conditions.

In example embodiments, the systems and methods of the present disclosure may be configured to determine at least one of (i) which of the biological parameters in the set have the greatest amount of uncertainty regarding the identification or quantification thereof or (ii) which of the biological parameters in the set are most deterministic of the identification or characterization of the one or more medical conditions. Thus, the systems and methods of the present disclosure may advantageously provide advice, e.g., relating to further diagnostics based on such determinations.

In example embodiments, the identifying and quantifying the set of biological properties utilizing the imaging data may include receiving patient data including the image data and parsing the received data into a set of empirical parameters including one or more imaging features of an imaged target. For example, the parsing the received data may include pre-processing image data including performing one or more of: (i) intensity vector analysis, (ii) image registration and transformation analysis or (iii) anatomic region analysis and imaging features may be derived derived based on one or more of: (i) temporal operators, (ii) fractal analysis, (iii) spatial operators or (iv) or an augmented Markov analysis.

In example embodiments, the set of biological properties may include one or more anatomical, morphological, structural, compositional, functional, chemical, biochemical, physiological, histological or genetic characteristics. In some embodiments, an imaged target may be a lesion and wherein the biological properties include (i) a size of the lesion, (ii) a shape of the lesion, (iii) a characterization of the margin of the lesion, (iv) a solidity of the lesion, (v) a heterogeneity of the lesion, (vi) a measure of the lesion's invasive extent or potential extent, (vii) a compositional measure of calcification related to the lesion and (viii) a measure of cell metabolism with respect to the lesion. In other embodiments, an imaged target may be a blood vessel and wherein the biological properties include (i) an indication of plaque coverage of the vessel wall, (ii) an indication of stenosis of the vessel wall, (iii) an indication of dilation of the vessel wall, and (iv) an indication of vessel wall thickness. In yet further embodiments, an imaged target may be a vascular tissue and wherein the biological properties include (i) an indication of a lipid core of the vascular or related tissue, (ii) a measure of fibrosis of the vascular or related tissue, (iii) a measure of calcification of the vascular or related tissue, (iv) an indication of any hemorrhage in the vascular or related tissue, (v) a measure of permeability of the vascular or related tissue, (vi) an indication of thrombosis of the vascular or related tissue, and (vii) an indication of ulceration of the vascular or related tissue. In some embodiments, at least one or the biological properties may be quantified by (i) assessing change between a plurality of timepoints or (ii) assessing differences between a plurality of targets.

In example embodiments, the characterization of the one or more medical conditions may include phenotyping the medical conditions. In some embodiments, the characterization of the one or more medical conditions may further include determining predictive outcomes for the medical conditions. For example, the one or more predictive outcomes may be predicated on a predetermined causality rating between phenotypes and the predictive outcomes.

In example embodiments, the storage medium may further include processor executable instructions implementing a trainer module, for training one or more algorithms implemented by the hierarchical analytics framework. In further example embodiments the storage medium may further include processor executable instructions implementing a cohort module for enabling a user to define one or more cohort groupings of individuals for further analysis.

In example embodiments, the analyzer module may include algorithms for calculating imaging features from the imaging data, wherein some of the imaging features are computed on a per-pixel basis, while other imaging features are computed on a region-of-interest basis. In some embodiments, the first set of algorithms is distinctly trained from the second set of algorithms. In example embodiments, at least one of the algorithms in the first and second sets of algorithms may be derived utilizing machine learning. For example, at least one of the algorithms in the first and second sets of algorithms may be characterized by one or more of neural nets, SVMs, partial least squares, principle components analysis or random forests.

In example embodiments, the analyzer module may be configured to enable delineating of a field for the imaging data. In some embodiment, the delineating the field may include segmenting one of organs, vessels, lesion or other application-specific anatomical features. For example, the field may be a cross-sectional slice of a blood vessel. In some embodiments, the analyzer module may be further configured to delineate a target in the field and determining anatomic structure or composition characteristics for the target, wherein the target is a blob in the cross-sectional slice of a blood vessel.

In example embodiments, the hierarchical analytics framework nay include fitting a biological model utilizing the imaging data wherein the biological model is then utilized to identify and quantify the biological properties. In some embodiments, the model may be a fractal model. In other embodiments, the model may be based on hybrid Bayesian/Markovian network. In example embodiments, the model may compute biological parameters one or more contiguous regions of a given analyte type. In some embodiments, the model may further compute biological parameters based on relationships between two- or more different contiguous regions of a given analyte type or given analyte types. In further embodiments, the model may also compute biological parameters based on a number of contiguous regions of a given analyte type or given analyte types. In some embodiments, the model may employ an expectation maximization which accounts for conditional dependence between pixels.

In example embodiments, a non-transient storage medium is disclosed including processor executable instructions for (i) receiving patient data including a set of empirical parameters, the set of empirical parameters including one or more imaging features of an imaged target; (i) utilizing a first algorithm to identify and quantify one or more logical characteristics indicated by the empirical parameters, the logical characteristics representing pathological features; (ii) identifying a set of pathological features, the set of pathological features including the one or more quantified logical characteristics; and (iii) utilizing a second algorithm to identify one or more pathologies indicated by the set of pathological features.

In example embodiments, the first algorithm may be derived utilizing a training collection of a plurality of sets of empirical parameters each with associated with known quantifications of one or more pathological features. In some embodiments, the first algorithm may include a scoring algorithm for determining a confidence weighting for each of the logical characteristics. For example, the confidence weighting for each logical characteristic may include a confidence weighting for a quantification of that logical characteristic. In some embodiments, the confidence weighting for the quantification of the logical characteristic may be determined according to a probability distribution across a range of values for the logical characteristic. In example embodiments, a confidence threshold may be utilized to identify the logical characteristics indicated by the empirical parameters.

In example embodiments, the second algorithm may include a scoring algorithm for determining a confidence weighting for each of the pathologies. For example, the confidence weighting for each pathology may include a confidence weighting for a phenotype thereof. In some embodiments, the confidence weighting for the phenotype may be determined according to a probability distribution across a range of phenotypes for the pathology. In example embodiments, a confidence threshold may be utilized to identify the pathologies indicated by the pathological features.

In example embodiments, an initial confidence weighting in a first pathology may be used to adjust an initial confidence weighting in a second related pathology. For example, an initial confidence weighting in the first pathology may be used to adjust an initial confidence weighting in a logical characteristic and wherein the adjusted confidence weighting in the logical characteristic may then be used to indicate the second related pathology.

In example embodiments, the first and second algorithms may be trained utilizing one or more of empirical data or expert opinion. In some embodiments, the first and second algorithms may be characterized by one or more of machine learning, decision trees, differential equations, polynomial expressions, pattern matching or parsing, dynamic programming, or state space searches.

In example embodiments, a system is disclosed the system including an imaging device for imaging a target; a processor configured for: (i) receiving patient data including a set of empirical parameters, the set of empirical parameters including one or more imaging features of the imaged target; (ii) utilizing a first machine learned algorithm to identify and quantify one or more logical characteristics indicated by the empirical parameters, the logical characteristics representing pathological features; (iii) identifying a set of pathological features, the set of pathological features including the one or more quantified logical characteristics; and (iv) utilizing a second machine learned algorithm to identify one or more pathologies indicated by the set of pathological features; and a user interface for outputting information relating to the one or more identified pathologies.

In example embodiments, a processor enabled method is disclosed, the method including identifying a set of empirical parameters, the set of empirical parameters including one or more imaging features of the imaged target; utilizing a first machine learned algorithm to identify and quantify one or more logical characteristics indicated by the empirical parameters, the logical characteristics representing pathological features; identifying a set of pathological features, the set of pathological features including the one or more quantified logical characteristics; and utilizing a second machine learned algorithm to identify one or more pathologies indicated by the set of pathological features.

While the systems and methods of the present disclosure have been particularly shown and described with reference to example embodiments thereof, it will be understood by those skilled in the art that various changes in form and details may be made therein without departing from the scope of the present disclosure.

BRIEF DESCRIPTION OF THE DRAWINGS

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments of the present disclosure.

DETAILED DESCRIPTION

Figure 1:
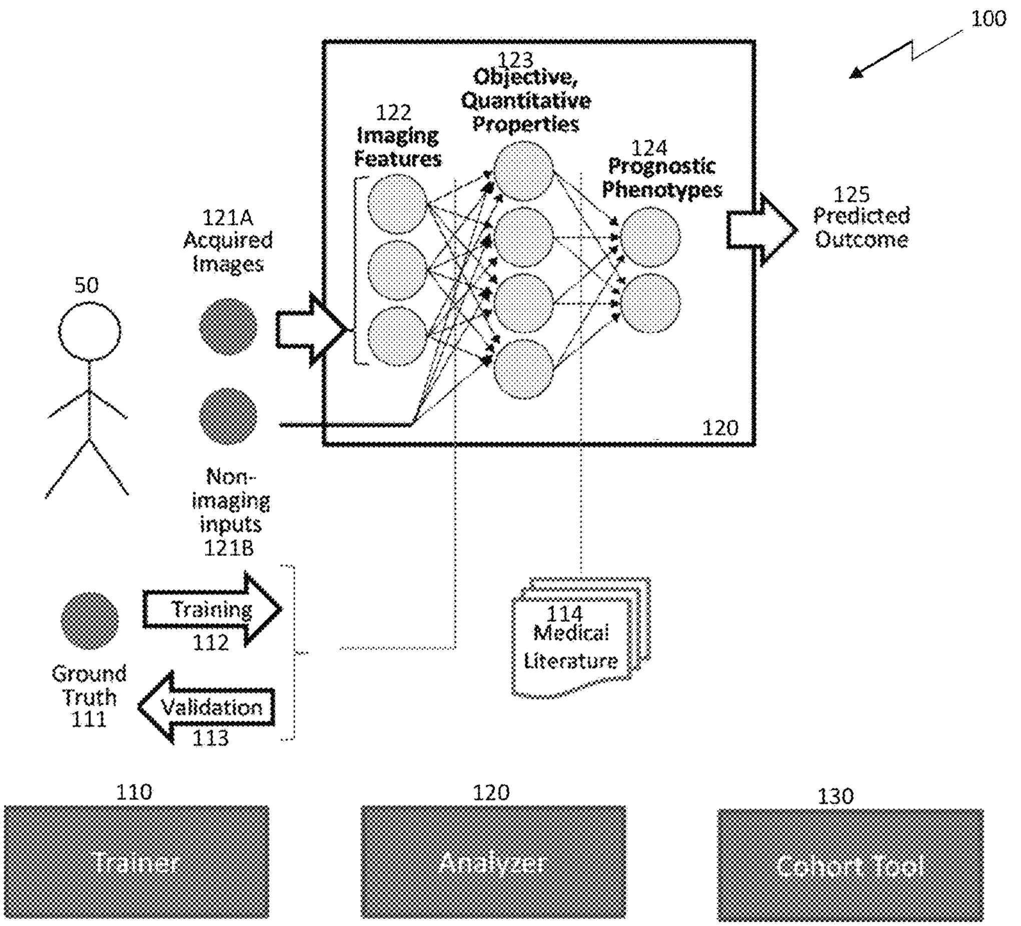
FIG. 1 depicts a schematic of an exemplary system for determining and characterizing a medical condition by implementing a hierarchical analytics framework, according to the present disclosure.

Systems and methods for analyzing pathologies utilizing quantitative imaging are presented herein. Advantageously, the systems and methods of the present disclosure utilize a hierarchical analytics framework that identifies and quantify biological properties/analytes from imaging data and then identifies and characterizes one or more pathologies based on the quantified biological properties/analytes. This hierarchical approach of using imaging to examine underlying biology as an intermediary to assessing pathology provides many analytic and processing advantages over systems and methods that are configured to directly determine and characterize pathology from underlying imaging data.

One advantage, for example, is the ability to utilize training sets from non-radiological sources, e.g., from tissue sample sources such as histological information, in conjunction with or independent of training sets for radiological sources, to correlate radiological imaging features to biological properties/analytes to pathologies. For example, in some embodiments, histology information may be used in training algorithms for identifying and characterizing one or more pathologies based on quantified biological properties/analytes. More specifically, biological properties/analytes which are identifiable/quantifiable in non-radiological data (such as in an invasively obtained histology data set or obtainable via gene expression profiling) may also be identified and quantified in radiological data (which is advantageously non-invasive). These biological properties/analytes may then be correlated to clinical findings on pathology using information the from non-radiological sources, for example, utilizing histological information, gene expression profiling, or other clinically rich data sets. This set of clinically correlated data may then serve as a training set or part of a training set for determining/tuning (e.g., utilizing machine learning) algorithms correlating biological properties/analytes to pathologies with a known relationship to clinical outcome. These algorithms correlating biological properties/analytes to pathologies derived utilizing non-radiological source training sets may then be applied in evaluating biological properties/analytes derived from radiological data. Thus, the systems and methods of the present disclosure may advantageously enable utilizing radiological imaging (which may advantageously be cost-effective and non-invasive) to provide surrogate measures for predicting clinical outcome.

Notably, in some instances training data for non-radiological sources (such as histology information) may be more accurate/reliable than training data for radiological sources. Moreover, in some embodiments, training data from non-radiological sources may be used to augment training data from radiological sources. Thus, since better data in is likely to yield better data out, the hierarchical analytics framework disclosed advantageously improves the trainability and resulting reliability of the algorithms disclosed herein. As noted above, one key advantage is that, once trained the systems and methods of the present disclosure may enable deriving comparable clinical information to existing histological and other non-radiological diagnostic-type testing without the need not undergo invasive and/or costly procedures.

Alternatively, in some embodiments, training sets for non-radiological sources (such as non-radiological imaging sources, e.g., histological sources, and/or non-imaging sources) may be utilized in conjunction with or independent of training sets for radiological sources, e.g., in correlating image features to biological properties/analytes. For example in some embodiments one or more biological models may be extrapolated and fitted to correlate radiological and non-radiological data. For example, histology information may be correlated with radiological information based on an underlying biological model. This, correlation may advantageously enable training recognition of biological properties/analytes in radiological data utilizing non-radiological, e.g., histological information.

In some embodiments, data drawn from complementary modalities may be used, e.g., in correlating image features to biological properties/analytes from blood panels and/or other sources of data.

In example embodiments one or more biological models may be extrapolated and fitted utilizing imaging data drawn from one imaging modality either correlated with and/or fused with another imaging modality or non-imaging source such as bloodwork. These biological models may advantageously correlate across and between imaging and non-imaging data sets based on the biological models. Thus, these biological models may enable the hierarchical analytics framework to utilize data from one imaging modality with another imaging modality or with a non-imaging source in identifying/quantifying one or more biological properties/analytes or identifying/characterizing one or more medical conditions.

Another advantage to the hierarchical analytics framework disclosed herein, is the ability to incorporate data from multiple same or different type data sources into the process of identifying and characterizing pathology based on imaging data. For example, in some embodiments, one or more non-imaging data sources may be used in conjunction with one or more imaging data sources in identifying and quantifying a set of biological properties/analytes. Thus, in particular, the set of biological properties/analytes may include one or more biological properties/analytes identified and/or quantified based on one or more imaging data sources, one or more biological properties/analytes identified and/or quantified based on one or more non-imaging data sources, and/or one or more biological properties/analytes identified and/or quantified based on a combination of imaging and non-imaging data sources (note that, for the purposes of the quantitative imaging systems and methods of the present disclosure the set of biological properties/analytes may generally include at least one or more biological properties/analytes identified and/or quantified based at least in part on an imaging data). The ability to augment information from an imaging data source with information from other imaging and/or non-imaging data sources in identifying and quantifying a set of biological properties/analytes adds to the robustness of the systems and methods presented herein and enables utilization of any and all relevant information in identifying and characterizing pathology.

Yet another advantage of the hierarchical analytics framework involves the ability to adjust/fine-tune data at each level, e.g., prior or subsequent to utilizing that data to assess the subsequent level (note that in some embodiments this may be an iterative process). For example, in some embodiments, information related to a set of identified and quantified biological properties/analytes may be adjusted in an a posteriori manner (e.g., after an initial identification and/or quantification thereof). Similarly, in some embodiments, information related to a set of identified and characterized pathologies may be adjusted in an a posteriori manner (e.g., after an initial identification and/or characterization thereof). These adjustments may be automatic or user based and may objective or subjective. The ability to adjust/fine-tune data at each level may advantageously improve data accountability and reliability.

In example embodiments, adjustments may be based on contextual information, which may be used to update one or more probabilities impacting a determination or quantification of a biological property/analyte. In example embodiments, contextual information for adjusting information related to a set of identified and quantified biological properties/analytes in an a posteriori manner may include patient demographics, correlations between biological properties/analytes or correlations between identified/characterized pathologies and biological properties/analytes. For example, in some instances the biological properties/analytes may be related in the sense that the identification/quantification of a first biological property/analyte may impact a probability relating the identification/quantification of a second biological property/analyte. In other instances, identification/characterization of a first pathology, e.g., based on an initial set of identified/quantified biological properties/analytes may impact a probability relating to the identification/quantification of a biological property/analyte in the initial set or even a biological property/analyte that wasn't in the first set. In further instances, pathologies may be related, e.g., wherein identification/characterization of a first pathology may impact a probability relating the identification/characterization of a first pathology. As noted above, information related to identification and quantification of biological properties/analytes and/or information related to the identification and characterization of pathologies may be updated in an iterative manner, e.g., until data convergence or thresholds/benchmarks are achieved or for a selected number of cycles.

A further advantage of the hierarchical analytics framework involves the ability to provide a user, e.g., a physician, with information relating both to a pathology as well as the underlying biology. This added context may facilitate clinical diagnosis/evaluation as well as assessing/determining next steps, e.g., therapeutic/treatment options or further diagnostics. For example, the systems and methods may be configured to determine which biological parameters/analytes relevant to the identification/quantification of one or more pathologies are most indeterminate/have the highest degree of uncertainty (e.g., by reason of lack of data or conflicting data). In such instances, specific further diagnostics may be recommended. The added context of providing a user with information relating both to a pathology as well as the underlying biology may further help the user evaluate/error check various the clinical conclusions and recommendations reached by the analytics.

A hierarchical analytics framework, as used herein, refers to an analytic framework wherein a one or more intermediary sets of data points are utilized as an intermediary processing layer or an intermediary transformation between initial set of data points and an end set of data points. This is similar to the concept of deep learning or hierarchical learning wherein algorithms are used to model higher level abstractions using multiple processing layers or otherwise utilizing multiple transformations such as multiple non-linear transformations. In general, the hierarchical analytics framework of the systems and methods of the present disclosure includes data points relating to biological properties/analytes as an intermediary processing layer or intermediary transformation between imaging data points and pathology data points, in example, embodiments, multiple processing layers or multiple transformation (e.g., as embodied by multiple levels of data points) may be included for determining each of imaging information, underlying biological information and pathology information. While example hierarchical analytic framework structures are introduced herein (e.g., with specific processing layers, transforms and datapoints), the systems and methods of the present disclosure are not limited to such implementations. Rather, any number of different types of analytic framework structures may be utilized without departing from the scope and spirit of the present disclosure.

In example embodiments, the hierarchical analytics frameworks of the subject application may be conceptualized as including a logical data layer as an intermediary between an empirical data layer (including imaging data)

and a results layer (including pathology information). Whereas the empirical data layer represents directly sourced data the logical data layer advantageously adds a degree of logic and reasoning which distills this raw data into a set of useful analytes for the results layer in question. Thus, for example, empirical information from diagnostics such as raw imaging information may be advantageously distilled down to a logical information relating to a particular set of biological features which is relevant for assessing a selected pathology or group of pathologies (for example, pathologies related to an imaged region of the patient's body). In this way the biological features/analytes of the subject application can also be thought of as pathology symptoms/indicators.

The biological features/analytes of the subject application may at times be referred to herein a biomarkers. While the term "biological" or prefix "bio" is used in characterizing biological features or biomarkers this in only intended to signify that the features or markers have a degree of relevance with respect to the patient's body. For example, biological features may be anatomical, morphological, compositional, functional, chemical, biochemical, physiological, histological, genetic or any number of other types of features related to the patient's body. Example, biological features utilized by specific implementations of the systems and methods of the present disclosure (e.g., as relating to particular anatomical regions of a patient such as the vascular system, the respiratory system, organs such as the lungs, heart or kidneys, or other anatomical regions) are disclosed herein.

While example systems and methods of the present disclosure may be geared toward detecting, characterizing and treating pathologies/diseases, the application of the systems and methods of the present disclosure are not limited to pathologies/diseases but rather may more generally applicable with respect to any clinically relevant medical conditions of a patient including, e.g., syndromes, disorders, traumas, allergic reactions, etc.

In exemplary embodiments, the systems and methods of the present disclosure relate to Computer-Aided Phenotyping, e.g., by using knowledge about biology to analyze medical images to measure the differences between disease types that have been determined through research to indicate phenotypes which in turn predict outcomes. Thus, in some embodiments, characterizing pathologies may include determining phenotypes for the pathologies which may in turn determine a predictive outcome.

With initial reference to FIG. 1, a schematic of an exemplary system 100 is depicted. There are three basic functionalities which may be provided by the system 100 as represented by the trainer module 110, the analyzer module 120 and the cohort tool module 130. As depicted, the analyzer module 120 advantageously implements a hierarchical analytics framework which first identifies and quantifies biological properties/analytes 130 utilizing a combination of (i) imaging features 122 from one or more acquired images 121A of a patient 50 and (ii) non-imaging input data 121B for a patient 50 and then identifies and characterizes one or more pathologies (e.g., prognostic phenotypes) 124 based on the quantified biological properties/analytes 123. Advantageously, the analyzer module 120 may operate independent of ground truth or validation references by implementing one or more pre-trained, e.g., machine learned algorithms for drawing its inferences.

In example embodiments, the analyzer may include algorithms for calculating imaging features 122 from the acquired images 121A of the patient 50. Advantageously, some of the image features 122 may be computed on a per-voxel basis while others may be computed on a region-of-interest basis. Example non-imaging inputs 121B which may be utilized along with acquired images 121A may include data from laboratory systems, patient-reported symptoms, or patient history.

As noted above, the image features 122 and non-imaging inputs may be utilized by the analyzer module 120 to calculate the biological properties/analytes 123. Notably, the biological properties/analytes are typically quantitative, objective properties (e.g., objectively verifiable rather than being stated as impression or appearances) that may represent e.g., a presence and degree of a marker (such as a chemical substance) or other measurements such as structure, size, or anatomic characteristics of region of interest. In example embodiments, the quantified biological properties/analytes 123 may be displayed or exported for direct consumption by the user, e.g., by a clinician, in addition to or independent of further processing by the analyzer module.

In example embodiments, one or more of the quantified biological properties/analytes 123 may be used as inputs for determining phenotype. Phenotypes are typically defined in a disease-specific manner independent of imaging, often being drawn from ex vivo pathophysiological samples for which there is documented relationship to outcome expected. In example embodiments, the analyzer module 120 may also provide predicted outcomes 125 for determined phenotypes.

It should be appreciated that example implementations of the analyzer module 120 are further described herein with respect to specific embodiments which follow the general description of the system 100. In particular, specific imaging features, biological properties/analytes and pathologies/phenotypes are described with respect to specific medical applications such as with respect to the vascular system or with respect to the respiratory system.

With reference still to FIG. 1, the cohort tool module 130 enables defining a cohort of patients for group analyses thereof, e.g., based on a selected set of criteria related to the cohort study in question. An example cohort analysis may be for a group of patient's enrolled in a clinical trial, e.g., with the patient's further being grouped based on one or more arms of the trial for example a treatment vs. control arm. Another type of cohort analysis may be for a set of subjects for which ground truth or references exist, and this type of cohort may be further decomposed into a training set or "development" set and a test or "holdout" set. Development sets may be supported so as to train 112 the algorithms and models within analyzer module 120, and holdout sets may be supported so as to evaluate/validate 113 the performance of the algorithms or models within analyzer module 120.

With continued reference to FIG. 1, the trainer module 110 may be utilized to train 112 the algorithms and models within analyzer module 120. In particular, the trainer module 110, may rely on ground truth 111 and/or reference annotations 114 so as to derive weights or models, e.g., according to established machine learning paradigms or by informing algorithm developers. In example embodiments, classification and regression models are employed which may be highly adaptable, e.g., capable of uncovering complex relationships among the predictors and the response. However, their ability to adapt to the underlying structure within the existing data can enable the models to find patterns that are not reproducible for another sample of subjects. Adapting to irreproducible structures within the existing data is commonly known as model over-fitting. To avoid building an over-fit model, a systematic approach may be applied that prevents a model from finding spurious structure and enable the end-user to have confidence that the final model will predict new samples with a similar degree of accuracy on the set of data for which the model was evaluated.

Successive training sets may be utilized to determine optimal tuning parameter(s), and a test set may be utilized to estimate an algorithm's or model's predictive performance. Training sets may be used for training each of the classifiers via randomized cross-validation. Datasets may be repeatedly split into training and testing sets and may be used to determine classification performance and model parameters. The splitting of the datasets into training and test sets occurs using a stratified or maximum dissimilarity approaches. In example embodiments a re-sampling approach (e.g. bootstrapping) may be utilized within the training set in order to obtain confidence intervals for (i) the optimal parameter estimate values, and (ii) the predictive performance of the models.

Figure 2:
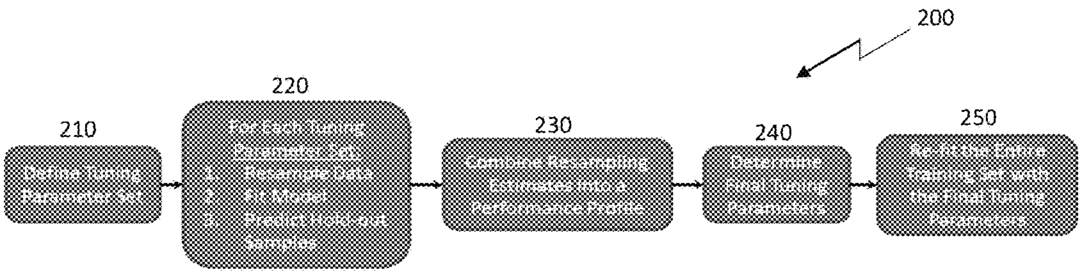
FIG. 2 outlines a re-sampling based model building approach, according to the present disclosure which may be implemented by the systems and methods described herein.

FIG. 2 outlines a re-sampling based model building approach 200 which may be utilized by the systems and methods of the present disclosure. First, at step 210, a tuning parameter set may be defined. Next, at step 220, for each tuning parameter set data is resampled the model is fitted and hold-out samples are predicted. At step 230, Resampling estimates are combined into a performance profile. Next, at step 240, final tuning parameters may be determined. Finally, at step 250, the entire training set is re-fitted with the final tuning parameters. After each model has been tuned from the training set, each may be evaluated for predictive performance on the test set. Test set evaluation occur once for each model to ensure that the model building process does not over-fit the test set. For each model that is constructed, the optimal tuning parameter estimates, the re-sampled training set performance, as well as the test set performance may be reported. The values of the model parameters over randomized splits are then be compared to evaluate model stability and robustness to training data.

According to the systems and methods of the present disclosure, a number of models may be tuned for each of the biological properties/analytes (e.g., tissue types) represented in ground truth maps. Model responses may include, for example, covariance based techniques, non-covariance based techniques, and tree based models. Depending on their construction, endpoints may have continuous and categorical responses; some of the techniques in the above categories are used for both categorical and continuous responses, while others are specific to either categorical or continuous responses. Optimal tuning parameter estimates, the re-sampled training set performance, as well as the test set performance may be reported for each model.

As model complexity grows, predictive performance often follows. This comes at the expense model interpretability. The parameter coefficients from a multiple linear regression model intuitively link each predictor to the response. The same kind of interpretation cannot be uncovered in a neural network, support vector machine, or many of the other models. However, these models may provide much better predictive ability, especially if the underlying relationship between the predictors and the response is non-linear. To tease out some interpretive information, variable importance calculations are performed. The main idea behind variable importance projection methods is that these techniques provide a weight to the individual features based on the extent that they contribute to a low dimensional data representation. For instance for problems where the number of features is equal to or larger than the number of training instances, classifier models can be subject to the "curse of dimensionality" problem. Techniques developed in conjunction with Principal component analysis (a linear dimensionality reduction method) to understand which predictors are most important for the underlying model and can direct the user to scientific connections between the predictors and the response.

TABLE 1

| | |
|---|---|
| Delineate Field | Register multiple data streams across a field<br>Segment organs, vessels, lesions, and other application-specific objects<br>Reformat anatomy for specific analyses |
| Delineate Target | Register multiple data streams at a locale<br>Fine-grained segmentation<br>Measure size and/or other relevant anatomic structure<br>Extract whole-target features |
| Delineate Sub-target regions | Split target into sub-targets according to application<br>Sub-target specific calculations |
| Delineate Components | (Re-) Segment Component<br>Calculate Readings<br>Visualize Probability Map |
| Determine Disease Severity | Determine Phenotype<br>Predict Outcome |
| Compare Multiple Timepoints | (Optional) Compare Multiple Timepoints |
| Assess multi-focal disease | Aggregate across target lesions over a wide scan field. |
| Generate Patient Report | Generate Patient Report |

Table 1, above, provides a summary of some of the example functionalities of the analyzer module 120 of system 100. Namely, the analyzer module 120 may be configured to delineate fields, for example, to register multiple data streams across a field; to segment organs, vessels, lesions and other application-specific objects; and/or to reformat/reconfigure anatomy for specific analyses. The analyzer module 120 may further be configured for delineating a target, for example, a lesion, in a delineated field. Delineating a target may, for example, include registering multiple data streams at a locale; conducting fine-grained segmentation; measuring size and/or other characteristics of relevant anatomic structures; and/or extracting whole-target features (e.g., biological properties/analytes characteristic of the entire target region). In some embodiments, one or more sub-target regions may also be delineated, for example, a target region may be split into sub-targets according to a particular application with sub-target specific calculations (e.g., biological properties/analytes characteristic of a sub-target region). The analyzer module 120 may also delineate components or relevant features (such as composition), for example, in a particular field, target or sub-target region. This may include segmenting or re-segmenting the components/features, calculating values for the segmented components/features (e.g., biological properties/analytes characteristic of the component/feature) and assigning a probability map to the readings. Next pathologies may be determined, based on the biological quantified properties/analytes, and characterized, e.g., by determining phenotype and/or predictive outcomes for the pathologies. In some embodiments, the analyzer module 120 may be configured to compare data across multiple timepoints, e.g., one or more of the biological components/analytes may involve a time based quantification. In further embodiments, a wide scan field may be utilized to assess multi-focal pathologies, e.g., based on aggregate quantifications of biological properties/analytes across a plurality of targets in the delineated field. Finally, based on the forgoing analytics, the analyzer module 120 may be configured to generate a patient report.

Figure 3:
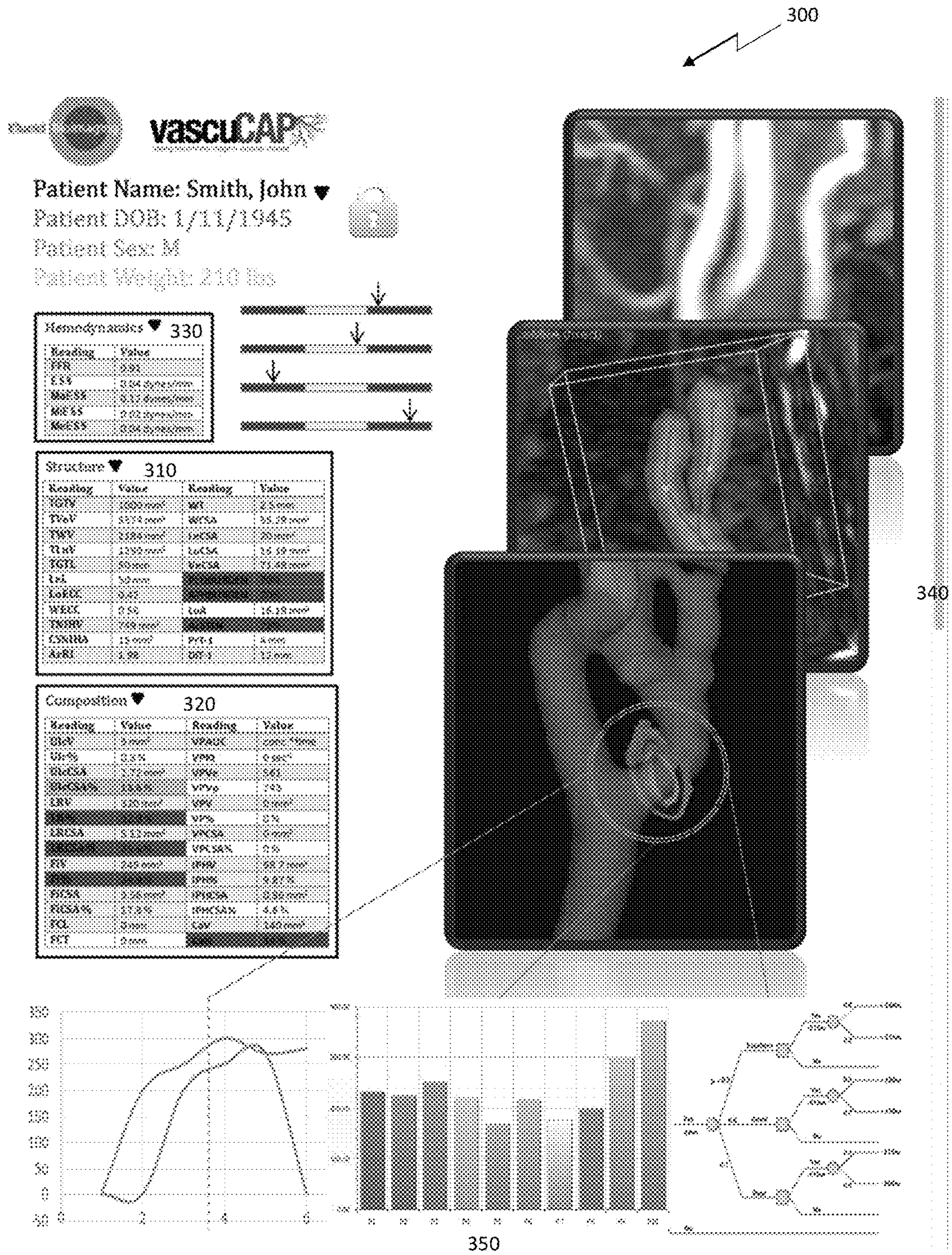
FIG. 3 depicts a sample patient report, according to the present disclosure which may be outputted by the systems and methods described herein.

A sample patient report 300 is depicted in FIG. 3. As shown, the sample patient report 300 may include quantifications of biological parameters/analytes such as relating to structure 310 and composition 320 as well as data from non-imaging sources such as hemodynamics 330. The sample patient report may further include visualizations 340, e.g., 2D and/or 3D visualizations of imaging data as well as combined visualizations of non-imaging data such as hemodynamic data overlaid onto imaging data. Various analytics 350 may be displayed for assessing the biological parameters/analytes including, e.g., a visualization of one or more model(s) (e.g., a decision tree model) for determining/characterizing pathology. Patient background and identifying information may further be included. Thus, the analyzer module 120 of system 100 may advantageously provide a user, e.g., a clinician with comprehensive feedback for assessing the patient.

Advantageously the systems and methods of the present disclosure may be adapted for specific applications. Example vascular and lung applications are described in greater detail in the sections which follow (although it will be appreciated that the specific application described have general implications and interoperability with respect to numerous other applications). Table 2 provides an overview of vascular and lung related applications utilizing a hierarchical analytics framework as described herein.

TABLE 2

| | Vascular Application | Lung Application |
|---|---|---|
| Modality | CT or MR | CT |
| Indication | Asymptomatic CAS<br>Cryptogenic stroke<br>NSTEMI, CABG Patency Evaluation<br>Companion-diagnostic for expensive or targeted drugs | Lung Cancer Screening<br>Drug therapy response assessment<br>Companion-diagnostic for expensive or targeted drugs |
| Diseases | Peripheral and coronary artery vasculopathy | Lung cancer first, then other pulmonary disease |
| Biological Properties | Structure<br>Composition<br>Hemodynamics<br>Gene Expression Correlates | Size, Shape/Margin<br>Solidity, Heterogeneity<br>Invasive Potential<br>Gene Expression Correlates |
| Extension | Ultrasound and/or multi-energy CT | PET and/or multi-energy CT |

The following sections provide specific examples of quantitative biological properties/analytes that may be utilized by the systems and methods of the present disclosure with respect to vascular applications:

Anatomic Structure:

Vessel structural measurements, specifically those that lead to the determination of % stenosis, have long been and remain the single most used measurements in patient care. These were initially limited to inner lumen measurements, rather than wall measurements involving both the inner and outer surfaces of the vessel wall. However, all of the major non-invasive modalities, unlike X-ray angiography, can resolve the vessel wall and with this come expanded measurements that may be achieved. The category is broad and the measurements are of objects of varying sizes, so generalizations should be made with care. A primary consideration is the limit of spatial sampling or resolution. The minimally detectable changes in wall thickness may, however, be lower than the spatial sampling by taking advantage of subtle variations in intensity levels due to partial volume effect. Additionally, stated resolutions generally refer to grid size and field of view of post-acquisition reconstructions rather than the actual resolving power of the imaging protocol, which determines the minimum feature size that can be resolved. Likewise, in-plane vs. through-plane resolutions may or may not be the same and not only the size of a given feature but as well its proportions and shape will drive the measurement accuracy. Last but not least, in some cases categorical conclusions are drawn from applying thresholds to the measurements, which may then be interpreted according to signal detection theory with the ability to optimize the trade-off between sensitivity and specificity, terms that don't otherwise refer to measurements in the normal sense.

Tissue Characteristics:

The quantitative assessment of the individual constituent components of the atherosclerotic plaques, including lipid rich necrotic core (LRNC), fibrosis, intraplaque hemorrhage, permeability, and calcification, can provide crucial information concerning the relative structural integrity of the plaque that could aid the physician's decisions on course of medical or surgical therapy. From the imaging technology point of view, the ability to do this lies less with spatial resolution as with contrast resolution and tissue discrimination made possible by differing tissues responding to incident energy differently so as to produce a differing receive signal. Each imaging modality does this to some extent; terms in ultrasound such as "echolucency", the CT number in Hounsfield Units, and differentiated MR intensities as a function of various sequences such as (but not limited to) T1, T2 and T2*.

Dynamic Tissue Behavior (e.g., Permeability):

In addition to morphological features of the vessel wall/plaque, there is increasing recognition that dynamic features are valuable quantitative indicators of vessel pathology. Dynamic sequences where the acquisition is taken at multiple closely-spaced times (known as phases) expand the repertoire beyond spatially-resolved values t include temporally-resolved values which may be used for compartment modeling or other techniques to determine the tissues' dynamic response to stimulus (such as but not limited to wash-in and wash-out of contrast agent). Through the use of dynamic contrast enhanced imaging with ultrasound or MR in the carotid arteries or delayed contrast enhancement in the coronary arteries, sensitive assessments of the relative permeability (e.g., Ktrans and Vp parameters from kinetic analysis) of the microvascular networks of neoangiogenesis within the plaques of interest can be determined. In addition, these dynamic series can also aid in the differentiation between increased vascular permeability versus intraplaque hemorrhage.

Hemodynamics:

The basic hemodynamic parameters of the circulation have a direct effect on the vasculopathy. Blood pressures, blood flow velocity, fractional flow reserve (FFR) and vessel wall shear stress may be measured by techniques ranging from very simple oscillometry to sophisticated imaging analysis. Using common principles of fluid dynamics, calculations of vessel wall shear stress can be ascertained for different regions of the wall. In similar fashion MRI, with or without the combination of US, has been used to calculate the wall shear stress (WSS) and correlate the results with structural changes in the vessel of interest. In addition, the effects of antihypertensive drugs on hemodynamics have been followed for short and long-term studies.

Thus, in example embodiments, key aspects of applying the systems and methods of the present disclosure in a vascular setting may include evaluating plaque structure and plaque composition. Evaluating plaque structure may advantageously include, e.g., lumen measurements (which improves stenosis measurement by providing area rather than only diameter measures) as well as wall measurements (e.g., wall thickness and vascular remodeling). Evaluating plaque composition may advantageously involve quantification of tissue characteristics (e.g., lipid core, fibrosis, calcification, and permeability) rather than just "soft" or "hard" designations as typically found in the prior art. Tables 3 and 4, below, describe example structural calculations and tissue characteristic calculations, respectively which may be utilized by the vascular applications of the systems and methods of the present disclosure.

TABLE 3

Structural calculations of vessel anatomy supported by vascular applications of the systems and methods disclosed herein.

| Measurand | Description | Type and Units |
|---|---|---|
| Remodeling Ratio | Calculated as the ratio of vessel area with plaque to reference vessel wall area without plaque | Expressed with value less than 1 for inward remodeling and greater than 1 for outward remodeling |
| % Stenosis | Calculated as the (1 − ratio of minimum lumen with plaque to reference lumen without plaque) × 100 both by area and by diameter | Expressed as percentage >0% |
| % Dilation | Calculated as the (ratio of maximum lumen with plaque to reference lumen without plaque − 1) × 100 both by area and diameter | Expressed as percentage >0% |
| Wall Thickness | Calculated by measuring the largest thickness of wall | Expressed in units of mm |

TABLE 4

Calculations of tissue characteristics supported by vascular applications of the systems and methods disclosed herein

| Measurand | Description | Type and Units |
|---|---|---|
| Lipid Core | The pathologic retention of lipids, particularly lipoproteins, by intimal/medial cells leading to progressive cell loss, cell death, degeneration, and necrosis. It is a mixture of lipid, cellular debris, blood and water in various concentrations. | Burden in $mm^2$ by cross section and $mm^3$ by target and vessel |
| Fibrosis | The pathologic and sometimes physiologic defensive production of fibrous tissue by fibroblasts and activated smooth muscle cells. | Burden in $mm^2$ by cross section and $mm^3$ by target and vessel |
| Calcification | The physiologic defensive biological process of attempting to stabilize plaque, which has a mechanism akin to bone formation. | Agatston score and burden in $mm^2$ by cross section and $mm^3$ by target and vessel |
| Hemorrhage | A pathologic component that may contribute to the vulnerability of a plaque. Its role is not fully understood, but it is believed to be a driving force in plaque progression through lipid accumulation from red blood cells. | Burden in $mm^2$ by cross section and $mm^3$ by target and vessel |
| Permeability | Described as endothelial and intimal permeability due to neovascularization, necrosis, collagen breakdown, and inflammation | Burden in $mm^2$ by cross section and $mm^3$ by target and vessel |
| Thrombosis | Local coagulation or clotting of the blood in a part of the circulatory system. | Degree |
| Ulceration | Disintegration and necrosis of epithelial tissue | Burden in $mm^2$ by cross section and $mm^3$ by target and vessel |

Example systems relating to evaluating the vascular system may advantageously include/employ algorithms for evaluating vascular structure. Thus, the systems may employ, e.g., a target/vessel segment/cross-section model for segmenting the underlying structure of an imaged vessel. Advantageously a fast marching competition filter may be applied to separate vessel segments. The systems may further be configured to handle vessel bifurcations. Image registrations may be applied utilizing Mattes mutual information (MR) or mean square error (CT) metric, rigid versor transform, LBFGSB optimizer, or the like. As noted herein, vessel segmentation may advantageously include lumen segmentation. An initial lumen segmentation may utilize a confidence connected filter (e.g., carotid, vertebral, femoral, etc.) to distinguish the lumen. Lumen segmentation may utilize MR imaging (such as a combination of normalized, e.g., inverted for dark contrast, images) or CT Data (such as use of registered pre-contrast, post-contrast CT and 2D Gaussian distributions) to define a lumenness function. Various connected components may be analyzed and thresholding may be applied. Vessel segmentation may further entail outer wall segmentation (e.g., utilizing a minimum curvature (k2) flow to account for lumen irregularities). In some embodiments, an edge potential map is calculated as outward-downward gradients in both contrast and non-contrast. In example embodiments, outer wall segmentation may utilize cumulative distribution functions (incorporating prior distributions of wall thickness, e.g., from 1-2 adjoining levels) in a speed function to allow for median thickness in the absence of any other edge information. In example embodiments, ferret diameters may be employed for vessel characterization. In further embodiments, wall thickness may be calculated as the sum of the distance to lumen plus the distance to the outer wall.

Example systems relating to evaluating the vascular system may further advantageously analyze vascular composition. For example, in some embodiments, composition may be determined based on image intensity and other image features. In some embodiments, the lumen shape may be utilized, e.g., as relating to determining thrombosis. Advantageously, an analyte blob model may be employed for better analyzing composition of particular sub-regions of the vessel. We define an analyte blob to be a spatially contiguous region, in 2D, 3D, or 4D images, of one class of biological analyte. The blob model may utilize an anatomically aligned coordinate system using isocontours, e.g., in normalized radial distance from the lumen surface to the adventitial surface of the vessel wall. The model may advantageously identify one or more blobs and analyze each blobs location e.g., with respect to the overall vessel structure as well as relative to other blobs. In example embodiments, a hybrid Bayesian/Markovian network may be utilized to model a relative location of a blob. The model may advantageously account for the observed image intensity at a pixel or voxel being influenced by a local neighborhood of hidden analyte category nodes thereby accounting for partial volume and scanner point spread function (PSF). The model may further allow for dynamically delineating analyte blob boundaries from analyte probability maps during inference by the analyzer module. This is a key distinction from typical machine vision approaches, such as with superpixel approaches, that pre-compute small regions to be analyzed but are unable to dynamically adjust these regions. An iterative inference procedure may be applied that utilizes uses the current estimate of both analyte probability and blob boundaries. In some embodiments parametric modeling assumptions or kernel density estimation methods may be used to enable probability density estimates between the sparse data used to train the model.

Introduced herein is a novel model for classification of composition of vascular plaque components that removes the requirements for histology-to-radiology registration. This model still utilizes expert-annotated histology as a reference standard but the training of the model does not require registration to radiological imaging. The multi-scale model computes the statistics of each contiguous region of a given analyte type, which may be referred to as a 'blob'. Within a cross-section through the vessel, the wall is defined by two boundaries, the inner boundary with the lumen and the outer boundary of the vessel wall, creating a donut shape in cross section. Within the donut shaped wall region, there are a discrete number of blobs (different than the default background class of normal wall tissue which is not considered to be a blob). The number of blobs is modeled as a discrete random variable. Then, each blob is assigned a label of analyte type and various shape descriptors are computed. Additionally, blobs are considered pairwise. Finally, within each blob, each pixel can produce a radiological imaging intensity value, which are modeled as independent and identically distributed (i.i.d.) samples that come from a continuously valued distribution specific to each analyte type. Note that in this last step, the parameters of the imaging intensity distributions are not part of the training process.

One key feature of this model is that it accounts for the spatial relationship of analyte blobs within the vessel and also to each other, recognizing that point-wise image features (whether from histology and/or radiology) is not the only source of information for experts to determine plaque composition. While the model allows for the ability to train without explicit histology-to-radiology registration, it could also be applied in situations where that registration is known. It is believed that statistically modeling the spatial layout of atherosclerotic plaque components for classifying unseen plaques is a novel concept.

Example techniques for estimating vessel wall composition from CT or MR images are further elaborated on in the following section. In particular, the methods may employ a multi-scale Bayesian analytic model. The basic Bayesian formulation is as follows:

$$P(A \mid I) = \frac{P(I \mid A) \cdot P(A)}{P(I)} \quad \text{posterior} = \frac{\text{likelihood} \cdot \text{prior}}{\text{evidence}}$$

In the context of the present disclosure, the hypothesis may be based on a multi-scale vessel wall analyte map, A, with observation combing from CT or MR image intensity information I.

Figure 4:
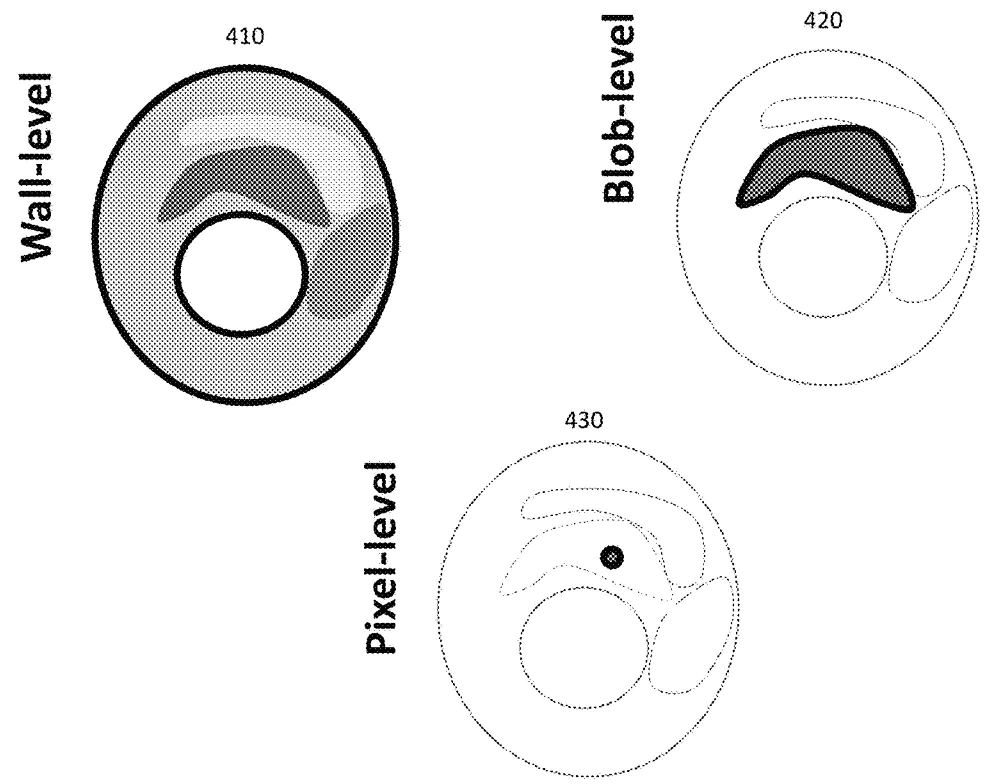
FIG. 4 depicts example segmentation levels for a multi-scale vessel wall analyte map, according to the present disclosure.

As depicted in FIG. 4, the multi-scale vessel wall analyte map may advantageously include wall-level segmentation 410 (e.g., a cross-sectional slice of the vessel), blob-level segmentation and pixel-level segmentation 430 (e.g., based on individual image pixels. E.g., A=(B,C) may be defined as a map of vessel wall class labels (similar to a graph with vertices B and edges C), wherein B is a set of blobs (cross-sectionally contiguous regions of non-background wall sharing a label) and C is a set of blob couples or pairs. $B_b$ may be defined as a generic single blob where $b \in [1 \ldots n_B]$ is an index of all blobs in A. $B_b^a$ is a blob with label a. For statistical purposes, the individual blob descriptor operator $D_B\{\ \}$ is in an low-dimensional space. $C_c$ may be defined as a blob pair where $c \in [1 \ldots n_B(n_B-1)/2]$ is an index of all blob pairs in A. $C_c^{f,g}$ is a blob pair with labels f and g. For statistical purposes, the blob pair descriptor operator $D_C\{\ \}$ is in a low-dimensional space. A(x)=a may be defined as the class label of pixel x where a∈{'CALC', 'LRNC', 'FIBR', 'IPH', 'background'} (compositional characteristics). In exemplary embodiments, I(x) is the continuous valued pixel intensity at pixel x. Within each blob, I(x) are modeled as independent. Note that because the model is used to classify wall composition in 3D radiological images, the word "pixel" is used to generically denote both 2D pixels and 3D voxels Characteristics of blob regions of like composition/structure may advantageously provide insights regarding the disease process. Each slice (e.g., cross-sectional slice) of a vessel may advantageously include a plurality of blobs. Relationships between blobs may be evaluated in a pairwise manner. The number of blobs within a cross-section is modeled as a discrete random variable and may also be of quantifiable significance. At the slice-level of segmentation, relevant characteristics (e.g., biological properties/analytes) may include a quantification of a total number of blobs and/or a number of blobs of a particular structure/composition classification; relationships between the blobs, e.g., spatial relationships such as being closer to the interior. At the blob level of segmentation, characteristics of each blob, such as structural characteristics, e.g., size and shape, as well as compositional characteristics, etc., may be evaluated serving as a biological properties/analytes. Finally at a pixel-level of segmentation, individual pixel level analysis may be performed, e.g., based image intensity distribution.

Probability mapping of characteristics may be applied with respect to the multi-scale vessel wall analyte map depicted in FIG. 4. The probability mapping may advantageously establish a vector of probabilities for every pixel with components of the vector for the probability of a each class of analyte and one component for the probability of background tissue. In example embodiments, sets of probability vectors may represent mutually exclusive characteristics. Thus, each set of probability vectors representing mutually exclusive characteristics will sum to 1. For example, in some embodiments, it may be known that a pixel should fall into one and only one compositional category (e.g., a single coordinate of a vessel cannot be both fibrous and calcified). Of particular note, the probability mapping does not assume independence of analyte class between pixels. This, is because neighboring pixels or pixels within a same blob may typically have same or similar characteristics. Thus, the probability mapping accounts, as described in greater detail herein, advantageously accounts for dependence between pixels.

$f(A=\alpha)$ may be defined as the probability density of map $\alpha$. f(A) is the probability distribution function over all vessel walls. $f(D_B\{B^a\}=\beta)$ is the probability density of descriptor vector $\beta$ with label a. $f(D_B\{B^a\})$ is the probability density function (pdf) of blob descriptors with label a. There is a probability distribution function for each value of a. $f(B)=\Pi f(D_B\{B^a\})$ $f(D_C\{C^{f,g}\}=\gamma)$ is the probability density of pairwise descriptor vector $\gamma$ with labels f and g. $f(D_c\{C^{f,g}\})$ is the probability density function (pdf) of pairwise blob descriptors. There is a probability distribution function for each ordered pair f,g. Thus:

$$f(C)=\Pi f(D_c\{C^a\})$$

$$f(A)=f(B)f(C)=\Pi f(D_b\{B^a\})\Pi f(D_c\{C^a\})$$

P(A(x)=a) is the probability of pixel x having label a. P(A(x)) is the probability mass function (pmf) of analytes (prevalence). It can be considered a vector of probabilities at a specific pixel x or as a probability map for a specific class label value.

Note that: $f(A)=P(N)\cdot f(C)\cdot f(B)=P(N)\cdot\Pi f(C_c)\cdot\Pi f(B_b)$ $f(C_c=\gamma)$ is the probability density of pairwise descriptor vector $\gamma$. $f(C_c)$ is the probability density function (pdf) of pairwise blob descriptors. $f(B_b=\beta)$ is the probability density of descriptor vector $\beta$. $f(B_b)$ is the probability density function (pdf) of blob descriptors. P(A(x)=a) is the probability of pixel x having label a. P(A(x)) is the probability mass function (pmf) of analytes (prevalence in a given map). It can be considered a vector of probabilities at a specific pixel x or as a spatial probability map for a specific analyte type. P(A(x)=a|I(x)=i) is the probability of analyte given the image intensity that is our main goal to compute. P(I(x)=i|A (x)=a) is the distribution of image intensities for a given analyte.

Figure 5:
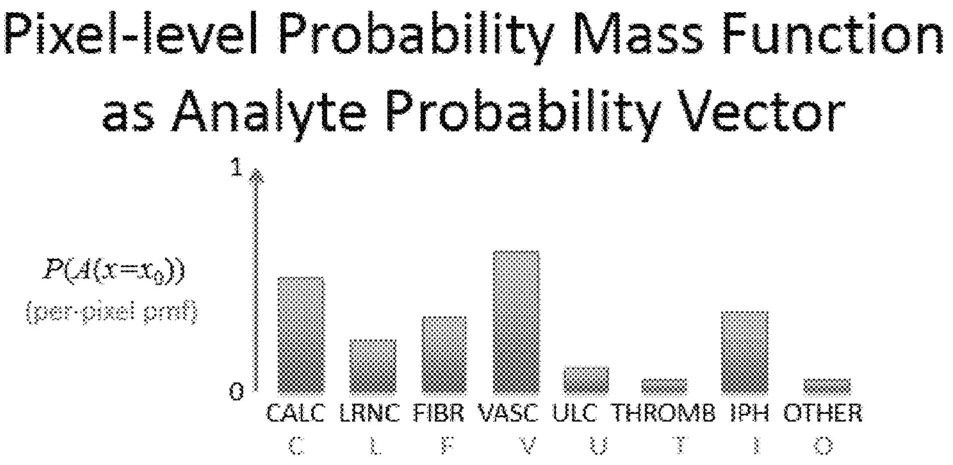
FIG. 5 depicts an exemplary pixel-level probability mass function as a set of analyte probability vectors, according to the present disclosure.

FIG. 5 depicts an exemplary pixel-level probability mass function as a set of analyte probability vectors. As noted above, the following assumptions may inform the probability mass function: Completeness: in example embodiments one may assume a sufficiently small pixel must fall into at least one of the analyte classes (including a catch-all 'background' category) and thus the sum of probabilities sums to 1. Mutual exclusivity: a sufficiently small pixel may be assumed to belong to only one class of analyte; if there are combinations (i.e., spiculated calcium on LRNC background), then a new combination class can be created in order to retain mutual exclusivity. Non-independence: each pixel may be assumed to be highly dependent on its neighbors and the overall structure of A.

An alternative view of the analyte map is as a spatial map of probability for a given analyte. At any given point during inference, analyte blobs can be defined using the full width half max rule. Using this rule, for each local maxima of probability for that analyte a region is grown outward to a lower threshold of half the local maxima value. Note that this 50% value is a tunable parameter. Spatial regularization of blobs can be done here by performing some curvature evolution on probability maps in order to keep boundaries more realistic (smooth with few topological holes). Note that different possible putative blobs of different analyte classes may in general have spatial overlap because until one collapses the probabilities these represent alternative hypotheses for the same pixel and hence the modifier 'putative'.

When iterative inference is terminated, there are several options for presentation of the results. First, the continuously valued probability maps can be presented directly to the user in one of several forms including but not limited to surface plots, iso-contour plots, or using image fusion similar to visualizing PET values as variation in hue and saturation on top of CT. A second alternative is to collapse the probability map at each pixel by choosing a single analyte label for each pixel. This can be done most straightforwardly by choosing the maximum a posteriori value at each pixel independently, thus creating a categorical map which could be visualized by assigning a distinct color to each analyte label and assigning either full or partial opacity on top of the radiological image. Under this second alternative, the label values might be assigned non-independently by resolving overlapping putative blobs based on a priority the probability of each blob. Hence, at a given pixel a lower priority analyte probability might be used for the label if it belongs to a higher probability blob.

Figure 6:
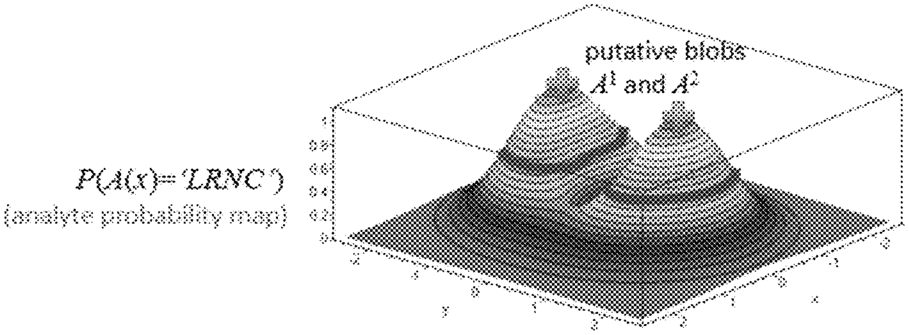
FIG. 6 illustrates a technique for computing putative analyte blobs, according to the present disclosure.

FIG. 6 illustrates a technique for computing putative analyte blobs. In example embodiments putative blobs may have overlapping regions. Thus, it may be advantageous to apply analytical techniques to segmenting pixels by putative blobs. For a probability of a given analyte the local maxima in probability is determined. The full width half max rule may then be applied to determine discrete blobs. At any given iteration of inference, analyte blobs can be defined using the full width half max rule. Find local maxima, then region grow with a lower threshold of 0.5*max. (The 50% value could be a tunable parameter.) In some embodiments, spatial regularization of blobs may also be applied, e.g., by performing some curvature evolution on probability maps in order to keep boundaries smooth and avoid holes. Note that at this stage different possible putative blobs of different analyte classes may, in general, have spatial overlap because until probabilities are collapsed these represent alternative hypotheses. Thus, an image-level analyte map be computed, e.g., based on a collapse of the probability map function. Notably, this collapse can be determined based on either the pixel-level analyte probability map, the putative blobs or a combination of both. With respect to the pixel-level analyte probability map, collapse can be determined by for each pixel, by choosing the label with maximum probability A(x):=arg maxa P(A(x)=a). This is similar to implementation Viterbi algorithm. Basically the highest probability for each set of mutually exclusive probabilities vectors is locked in (e.g. with analyte priorities breaking possible ties). All other probabilities in the set may then be set to zero. In some embodiments, probabilities for neighboring pixels/regions may be taken into account when collapsing data on a pixel level. With respect to putative blob level collapse, overlapping putative blobs may be resolved. In some embodiments, prioritization can be based on blob probability density $f(D_1\{A_a^b\}=d_1)$. Since higher probability blobs may change shape of overlapped lower probability blob this may impact analysis of blob level characteristics. In example embodiments, the full range of probabilities may be maintained rather than collapsing the data.

In order to model the relative spatial positioning of blobs within the vessel wall, an appropriate coordinate system can be chosen in order to provide rotational-, translational-, and scale-invariance between different images. These invariances are important to the model because they allow the ability to train on one type of vessel (e.g., carotids where endarterectomy specimens are easily available) and apply the model to other vessel beds (e.g., coronary where plaque specimens are generally not available) under the assumption that the atherosclerotic process is similar across different vessel beds. For tubular objects, a natural coordinate system follows from the vessel centerline where distance along the centerline provides a longitudinal coordinate and each plane perpendicular to the centerline has polar coordinates of radial distance and angle. However, due to the variability of vessel wall geometry, especially in the diseased patients, which one may aim to analyze, an improved coordinate system may be utilized. The longitudinal distance is computed in a way so that each 3D radiological image pixel is given a value, not just along the centerline or along interpolated perpendicular planes. For a given plaque, the proximal and distal planes perpendicular to the centerline are each used to create an unsigned distance map on the original image grid, denoted P(x) and D(x), respectively where x represents the 3D coordinates. The distance map $l(x)=P(x)/(P(x)+D(x))$, represents the relative distance along the plaque with a value of 0 at the proximal plane and 1 at the distal plane. The direction of the l-axis is determined by $\nabla l(x)$.

Because the geometry of the wall may be significantly non-circular, the radial distance may be defined based on the shortest distance to the inner luminal surface and the shortest distance to the outer adventitial surface. The expert-annotation of the histology images includes regions that define the lumen and the vessel (defined as the union of the lumen and vessel wall). A signed distance function can be created for each of these, L(x) and V(x), respectively. The convention is that the interior of these regions is negative so that in the wall L is positive and V is negative. The relative radial distance is computed as $r(x)=L(x)/(L(x)-V(x))$. It has a value of 0 at the luminal surface and 1 at the adventitial surface. The direction of the r-axis is determined by $\nabla r(x)$.

Because of the non-circular wall geometry, the normalized tangential distance may be defined as lying along iso-contours of r (and of l if processing in 3D). The direction of the t-axis is determined by $\nabla r \times \nabla l$. The convention is that histology slices are assumed to be viewed looking from the proximal to the distal direction so that positive l points into the image. Note that unlike the others, t does not have a natural origin since it wraps onto itself around the vessel. Thus, one can define the origin of this coordinate differently for each blob relative to the centroid of the blob.

Another wall coordinate that is used is normalized wall thickness. In some sense, this is a proxy for disease progression. Thicker wall is assumed to be due to more advanced disease. Assumption that statistical relationship of analytes changes with more advanced disease. The absolute wall thickness is easily calculated as $w_{abs}(x)=L(x)-V(x)$. In order to normalize it to the range of [0-1], one may determine that maximum possible wall thickness when the lumen approaches zero size and is completely eccentric and near the outer surface. In this case the maximum diameter is the maximum Feret diameter of the vessel, $D_{max}$. Thus the relative wall thickness is computed as $w(x)=w_{abs}(x)/D_{max}$.

The degree to which the aforementioned coordinates may or may not be used in the model is in part dependent on the amount of training data available. When training data is limited, several options are available. The relative longitudinal distance may be ignored treating different sections through each plaque as though they come from the same statistical distribution. It has been observed that plaque composition changes along the longitudinal axis with more severe plaque appearance in the middle. However, instead of parameterizing the distributions by l(x), this dimension can be collapsed. Similarly, the relative wall thickness may also be collapsed. Observations have been made that certain analytes occur in "shoulder" regions of plaques where w(x) would have a middle value. However, this dimension can also be collapsed until enough training data is available.

Figure 7:
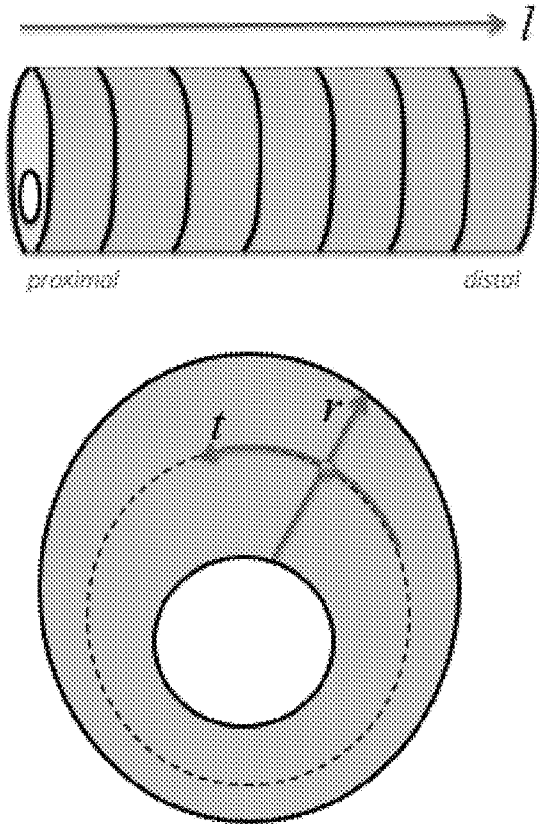
FIG. 7 depicts normalized vessel wall coordinates for an exemplary vessel wall composition model, according to the present disclosure.

As noted above, a vessel wall composition model may be utilized as the initial hypothesis (e.g., at the prior P(A)). FIG. 7 depicts normalized vessel wall coordinates for an exemplary vessel wall composition model. In the depicted model, l is relative longitudinal distance along vessel target from proximal to distal, which may be calculated, e.g., on a normalized the interval [0,1]. The longitudinal distance may be computed with 2 fast marching propagations starting from proximal and from distal planes to compute unsigned distance fields P and D wherein $l=P/(P+D)$. l-axis direction is $\nabla l$. As depicted, r is normalized radial distance which may also be calculated on a normalized interval [0,1] from luminal to adventitial surface. Thus, $r=L/(L+(-V))$ where L is lumen signed distance field (SDF) and V is vessel SDF. r-axis direction is $\nabla r$. Finally, t is normalized tangential distance which may be computed, e.g., on a normalized interval [−0.5,0.5]. Notably, in example embodiments there is may be no meaningful origin for the entire wall, only for individual analyte blobs (thus, t origin may be at blob centroid). The tangential distance is computed along iso-contour curves of l and of r. t-axis direction is $\nabla r \times \nabla l$.

Figure 9:
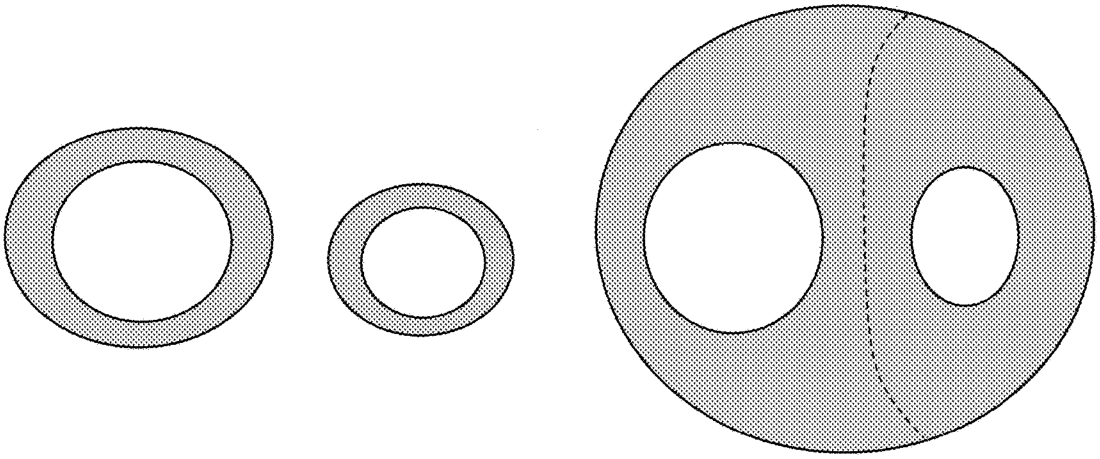
FIG. 9 illustrates some complex vessel topologies which can be accounted for using the techniques described herein, according to the present disclosure.

FIG. 9 illustrates some complex vessel topologies which can be accounted for using the techniques described herein. In particular, when processing CT or MR in 3D, different branches may be advantageously analyzed separately so that the relationship between analyte blobs in separate branches are properly ignored. Thus, if a segmented view (cross-sectional slice) If includes more than one lumen, one can account for this by performing a watershed transform on r in order to split up wall into domains belonging to each lumen after which each domain may be separately considered/analyzed.

As noted above, many of the coordinates and probability measurements described herein may be represented utilizing normalized scales thereby preserving scale invariance, e.g., between different sized vessels. Thus, the proposed model may advantageously be independent of absolute vessel size, under the assumption that a disease process is similar and proportional for different caliber vessels.

In some embodiments, the model may be configured to characterize concentric vs. eccentric plaque. Notably, a normalized all thickness close to 1 may indicate highly eccentric place. In further embodiments, inward vs. outward plaque characterization may be implemented. Notably, histological information on this characteristic is hindered by deformation. Thus, in some embodiments, CT and training data may be utilized to establish an algorithm for determining inward vs. outward plaque characterization.

Figure 8:
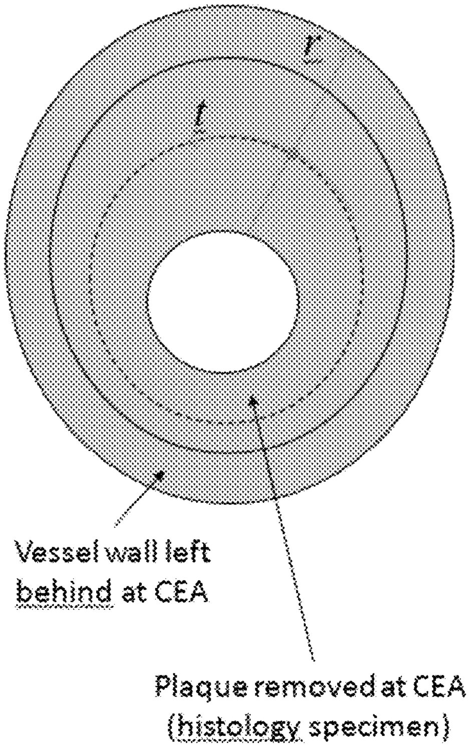
FIG. 8 depicts an example margin between plaque removed for a histology specimen and the outer vessel wall, according to the present disclosure.

As noted above, in example embodiments, non-imaging data, such as histology data, may be utilized as a training set for establishing algorithms linking image features to biological properties/analytes. There are however, some differences between the data types that need to be addressed in ensuring a proper correlation. For example, the following differences between histology and imaging may impact proper correlation: Carotid endarterectomy (CEA) leaves adventitia and some media behind in patient CT or MR image analysis presumed to find outer adventitial surface. (See e.g., FIG. 8 depicting the margin between the plaque removed for the histology specimen relative to the outer vessel wall). Notably, scientific literature shows uncertainty of whether calcification can occur in adventitia. The following techniques may be employed to account for this difference. Histology can be dilated outward, e.g., based on an assumption that little to no analyte in the wall is left behind. Alternatively, Image segmentation can be eroded inward, e.g., based on knowledge of typical or particular margins left. For example, an average margin may be utilized. In some embodiment an average margin may be normalized a percentage of the overall diameter of the vessel. In further embodiments, histology may be used to mask the imaging (e.g., overlay, based on alignment criteria). In such embodiments it may be necessary to apply one or more transformations to the histology data to match proper alignment. Finally, in some embodiments, the difference may be ignored (which is equivalent to uniform scaling of removed plaque to entire wall). While this may induce some small error, presumably the wall left behind may be thin compared to plaque in CEA patients.

Longitudinal differences may also exist between histological data (e.g., a training set) and the imaging data as represented by the vessel wall composition model. In example embodiments, longitudinal distance may be modeled/correlated explicitly. Thus, e.g., histology slice numbering (A-G for example) can be used to roughly determine position within excised portion of plaque. This approach, however, limits analysis with respect to other slices without corresponding histology data. Thus, alternatively, in some embodiments, all histology slices may be treated as arising from the same distribution. In example embodiments, some limited regularization may still be employed along the longitudinal direction.

As noted above, normalized wall thickness, in some sense is an imperfect proxy for disease progression. In particular, a thicker wall is assumed to be due to more advanced disease, e.g. based on an assumption that statistical relationship of analytes changes with more advanced disease. Normalized wall thickness may be calculated as follows: An absolute wall thickness $T_a$ may be determined (in mm), e.g., computed as $T_a=L+(-V)$ where L is lumen SDF, V is vessel SDF and $D_{max}$ is maximum Feret diameter of vessel (in mm). A relative wall thickness T may then be computed based on $T=T_a/D_{max}$, e.g., on an interval [0,1], where 1 indicates thickest part of small lumen indicative of completely eccentric plaque. In example embodiments, probabilities may be conditioned based on wall thickness, e.g., so that the distribution of analyte blobs would depend on wall thickness. This advantageously may model differences in analyte composition over the course of disease progression.

Figure 10:
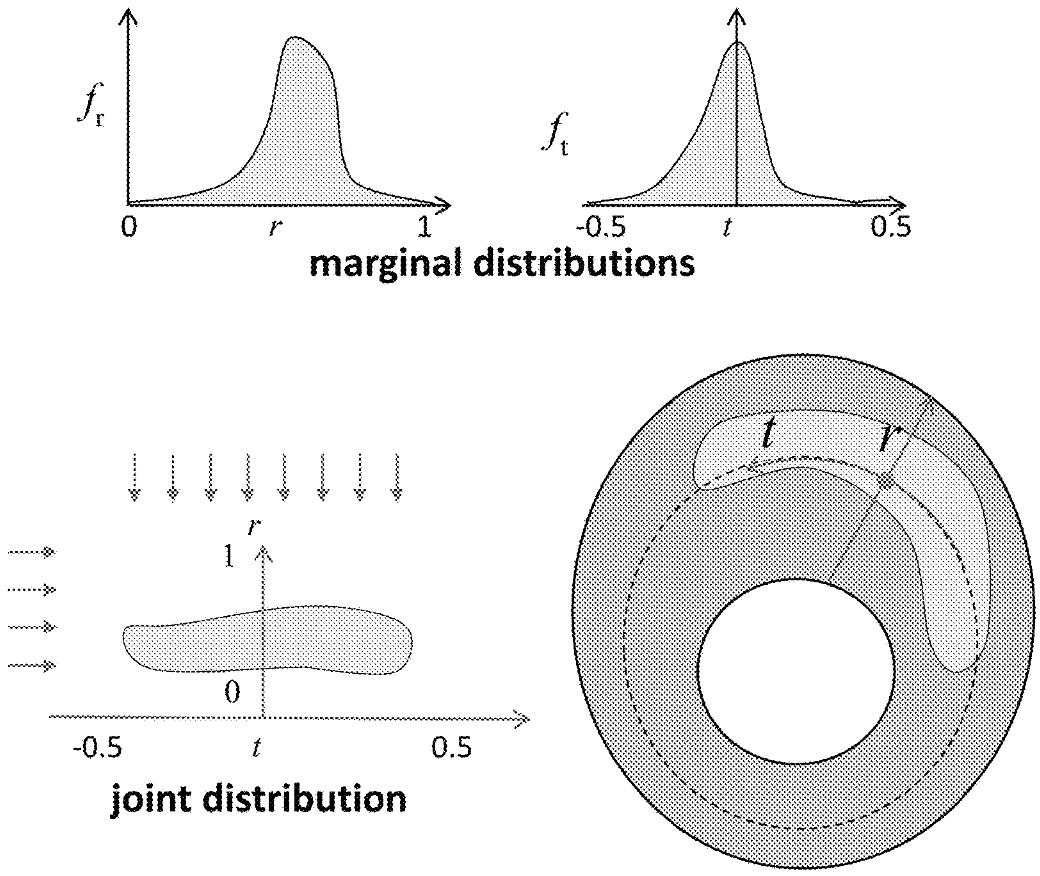
FIG. 10 depicts representing an exemplary analyte blob with a distribution of normalized vessel wall coordinates, according to the present disclosure.

FIG. 10 depicts representing an exemplary analyte blob with a distribution of normalized vessel wall coordinates. In particular, the origin oft is placed at blob centroid. (r,t) coordinates are a random vector where the location/shape is fully represented by the joint distribution of points within. This can be simplified by considering the marginal distributions (since radial and tangential shape characteristics seem relatively independent). Marginal distributions may be calculated as projections along r and t (note that l and T coordinates can also be considered). Notably, the marginal distribution in the radial direction may advantageously represent/characterize the plaque growth in concentric layers (e.g., medial layer, adventitial layer and intima layer.) Similarly, the marginal distribution in the tangential direction may advantageously represent a growth factor which may be indicative of the staging of the disease. In example embodiments, analyte blob descriptors can be computed based on the marginal distributions. For example, on can take low order statistics on the marginal distributions (or use histograms or fit parametric probability distribution functions).

In example embodiments, the following analyte blob descriptors may be used, e.g., to capture location, shape or other structural characteristics of individual blobs:

- Location in normalized vessel coordinates
  - Mostly with respect to r
    - e.g., in order to distinguish between shallow/deep calcification
  - t-direction ignored; [optionally model l-direction]
- Extent in normalized vessel coordinates
  - Intentionally avoiding the word 'size' which implies an absolute measurement, whereas extent is a normalized value
- Lopsidedness to represent degree of asymmetry in distribution
  - Clinical significance is unclear but it may help to regularize shapes against implausible lopsided shapes
- Alignment to represent confinement to parallel tissue layers
  - Analyte blobs seem to stay within radial layers (iso-contours of r) quite well so this will help select image processed shapes that are similar
- Wall thickness where the blob is located
  - Thick (i.e., advanced) plaques assumed to have different statistics than thin plaques In some embodiments, pair-wise blob descriptors may also be utilized. For example:

- Relative location
  - e.g., if fibrosis is on the lumen side of LRNC
- Relative extent
  - e.g., how thick/wide is fibrosis relative to LRNC
- Surroundedness
  - How much one marginal projection falls close to the middle of the other
  - e.g., napkin ring sign or fibrosis around LRNC
- Relative wall thickness
  - To represent degree of 'shoulderness' (shoulder would be relatively less thick than central plaque body)

It is noted that higher order interactions (e.g., between three blobs or between two blobs and another feature), may also be implemented. However, consideration may be given to diminishing returns and training limitations.

The following are example quantifications of blob descriptors:

Individual blob descriptors

| | | |
|---|---|---|
| Location | $\alpha_r = E[r]$ | |
| Extent | $\beta_r = Var[r]$ | $\beta_t = Var[t]$ |
| Lopsidedness | $\gamma_r = \lvert Skewness[r] \rvert$ | $\gamma_t = \lvert Skewness[t] \rvert$ |
| Alignment | $\delta_r = Kurtosis[r]$ | $\delta_t = Kurtosis[t]$ |
| Thickness | $\tau_T = E[T]$ | |

Pairwise blob descriptors

| | | |
|---|---|---|
| Relative location | $\alpha_{rr} = E[r_2] - E[r_1]$ | $\alpha_{tt} = E[t_2] - E[t_1]$ |
| Relative extent | $\beta_{rr} = Var[r_2]/Var[r_1]$ | $\beta_{tt} = Var[t_2]/Var[t_1]$ |
| Surroundedness | $\varepsilon_{rr} = \|\alpha_{rr}\|\beta_{rr}$ | $\varepsilon_{tt} = \|\alpha_{tt}\|\beta_{tt}$ |
| Relative thickness | $\tau_{TT} = E[T_2]/E[T_1]$ | |

Figure 11:
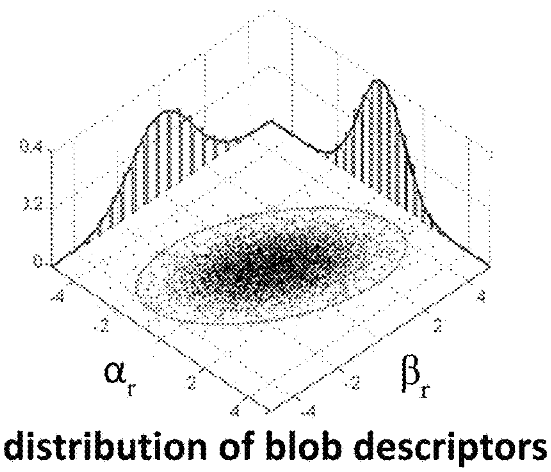
FIG. 11 depicts an exemplary distribution of blog descriptors, according to the present disclosure.

Notably, the set of descriptors (e.g., 8-12 descriptors) form a finite shape space that a blob lives in. One can then look at the distribution of a population of blobs as a distribution in this finite space. FIG. 11 depicts an exemplary distribution of blog descriptors. In example embodiments the distribution of blob descriptors may be computed over the whole training set. In some embodiments, lower order statistics may be utilized on individual blob descriptors (assuming independence), e.g., Location: $E[\alpha_r]$, $Var[\alpha_r]$. In other embodiments, a multidimensional Gaussian (mean vector+covariance matrix) analysis may be used to model the descriptors (e.g., wherein independence is not assumed). In further embodiments, if the distribution is non-normal it may be modeled with density estimation techniques.

Figure 14:
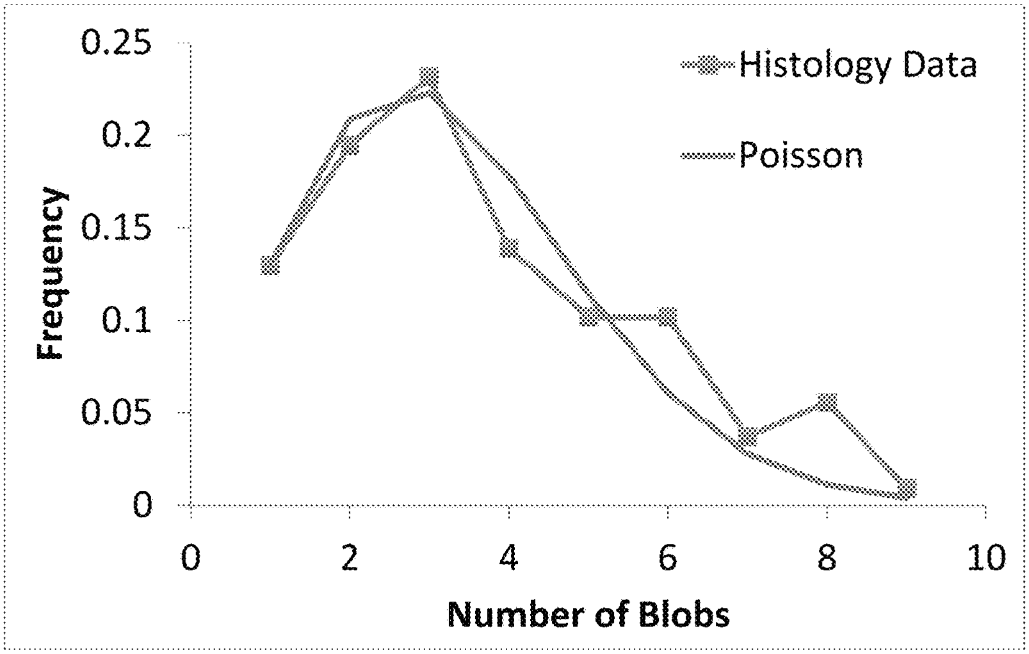
FIG. 14 depicts an example frequency distribution of total number of blobs per histological slide for a plurality of histological slides, according to the present disclosure.

As noted above, one can also model a number of blobs per cross section (or the number of each class), e.g., $\eta$ without regard to analyte class and $\eta_i$ counting number in each analyte class. FIG. 14 depicts frequency distribution of the total number of blobs for each histology slide. A poison regression is applied as an overly. Note that the analytic chart of FIG. 14 depicts the number of blobs per cross section N without regard to analyte class (number of blobs of each analyte type is represented by B).

Summarizing the forgoing sections, in example embodiments, the overall vessel wall composition model may include the following:

Per-pixel analyte prior pmf $$P(A(x)=a_i)=\rho_i$$

Individual blob descriptors $$B_1=(\alpha_r,\beta_r,\beta_t,\gamma_r,\gamma_t,\delta_r,\delta_t,\tau_T)$$

$$B_1\sim N(\mu_1,\Sigma_1)$$

Pairwise blob descriptors $$C_2=(\alpha_{rr},\alpha_{tt},\beta_{rr},\beta_{tt},\varepsilon_{rr},\varepsilon_{tt},\tau_{TT})$$

$$C_2\sim N(\mu_2,\Sigma_2)$$

Number of blobs $$\eta\sim \text{Poisson}(\lambda_\eta)$$

wherein:

$$P(A(x)=a_i)=\rho_i$$

$$f(A^b)=f(B_1{}^b)$$

$$f(A) = P(\eta)\cdot\left(\prod_{b\neq c} f(C_2^{bc})\right)\cdot\prod_b f(A^b)$$

Figure 12:
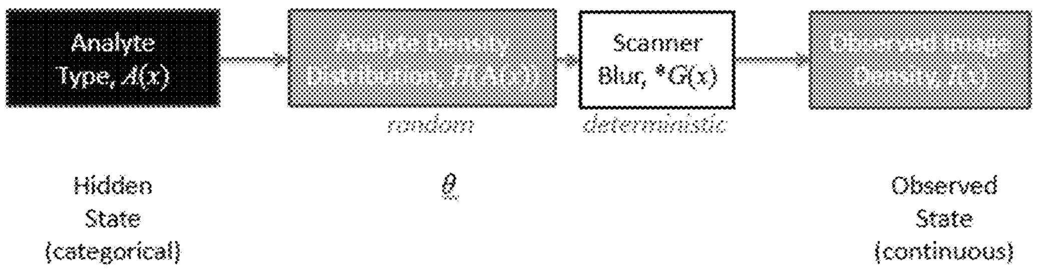
FIG. 12 depicts an exemplary model for imaging data correlating between a hidden ground truth state and an observed state, according to the present disclosure.

As noted above, an imaging model may serve as an the likelihood (e.g., P(I\A)) for the Bayesian analytic model. A maximum likelihood estimate may then be determined. In example embodiments, this may be done considering each pixel in isolation (e.g., without regard to the prior probability of the structure in the model). Estimated analyte maps are typically smooth only because images are smooth (which is why no prior smoothing is typically performed). Independent pixel-by-pixel analysis can be done, e.g., at least up to the point of accounting for scanner PSF. The imaging model is utilized to account for imperfect imaging data. For example, imaging small components of plaque adds independent noise on top of pixel values. Moreover, the partial volume effect and scanner PSF are well known as applying to small objects. Thus, given a model (e.g., level set representation of analyte regions), simulating CT by Gaussian blurring with PSF is easy and fast. The imaging model described herein may also be applied to determine (or estimate) the distribution of true (not blurred) densities of different analytes. Notably this cannot come from typical imaging studies since these will have blurred image intensities. In some embodiments, wide variances could be used to represent the uncertainty. Alternatively, distribution parameters could be optimized from training set but the objective function would have to be based on downstream readings (of analyte areas), e.g., unless aligned histology data is available. FIG. 12 depicts the exemplary model for imaging data (e.g., correlating between a hidden (categorical) state (A(x)) and an observed (continuous) state (I(x)) whereby random (e.g., analyte density distribution (H(A (x))) and deterministic (e.g., scanner blur *G(x)) noise factors are accounted for. $\theta$ are the parameters of H (proportion & HU mean/variance of each analyte). $\theta=(\tau_1, \mu_1, \sigma_1, \ldots, \tau_N, \mu_N, \sigma_N)$ for N different analyte classes assuming normal distributions. Note that $\theta$ are patient specific and will be estimated in an expectation maximization (EM) fashion, e.g., wherein analyte labels are the latent variables and the image is observed data.

E-step: determine membership probabilities given current parameters

M-step: maximize likelihood of parameters given membership probabilities

Figure 13:
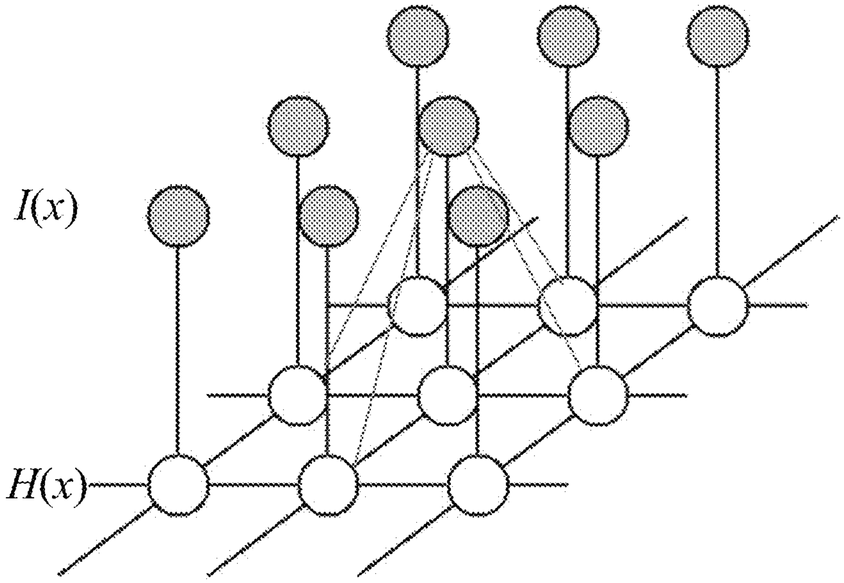
FIG. 13 depicts a diagram of an example Markov model/Viterbi algorithm for relating an observed state to a hidden state in an image model, according to the present disclosure.

FIG. 13 depicts a diagram of an example Markov model/Viterbi algorithm for relating an observed state to a hidden state in an image model. In particular, the diagram depicts an observed state (gray) (observed image intensity, I(x)) and a hidden state (white) (pure analyte intensity, H(A(x))) which can be modeled either with empirical histogram or with Gaussian or boxcar probability distribution function. PSF of imaging system is modeled as Gaussian, G(x). Thus, $$I(x)=G(x)*H(A(x))$$

It is noted that a Viterbi-like algorithm could apply here but convolution would replace emission probabilities H could be modeled as Gaussian or uniform.

As noted above, one portion of the inference procedure is based upon expectation maximization (EM). In a typical application of EM, data points are modeled as belonging to one of several classes, which is unknown. Each data point has a feature vector and for each class, this feature vector may be modeled with a parametric distribution such as a multidimensional Gaussian, represented by a mean vector and a covariance matrix. In the context of the model presented herein, a straightforward EM implementation would work as follows:

$$L(\theta; I) = \prod_{x=1}^{N_{pixels}} \sum_{a=1}^{N_{analytes}} \tau_a G(I(x); \mu_a, \sigma_a) \text{ where}$$

$G$ is Gaussian function

-continued $$L(\theta; I, A) = p(I, A \mid \theta)$$

$$= \prod_{x=1}^{N_{pixels}} \sum_{a=1}^{N_{analytes}} \delta_{a,A(x)} \tau_a G(I(x); \mu_a, \sigma_a)$$

where $\delta$ is Kronecker delta $$= \exp\left\{ \sum_{x=1}^{N_{pixels}} \sum_{a=1}^{N_{analytes}} \delta_{a,A(x)} \left[ \ln\tau_a - \frac{\ln(2\pi\sigma_a^2)}{2} - \frac{(I(x) - \mu_a)^2}{2\sigma_a^2} \right] \right\}$$

$$T_{j,x}^{(t)} := P(A(x) = j \mid I = I(x); \theta^{(t)}) = \frac{\tau_j^{(t)} G(I(x); \mu_j^{(t)}, \sigma_j^{(t)})}{\sum_{a=1}^{N_{analytes}} \tau_a^{(t)} G(I(x); \mu_a^{(t)}, \sigma_a^{(t)})}$$

(membership probabilities)

$$Q(\theta \mid \theta^{(t)}) = E[\ln L(\theta; I, A)]$$

$$= E\left[ \ln \prod_{x=1}^{N_{pixels}} L(\theta; I(x), A(x)) \right]$$

$$= \sum_{x=1}^{N_{pixels}} E[\ln L(\theta; I(x), A(x))]$$

$$= \sum_{a=1}^{N_{analytes}} \sum_{x=1}^{N_{pixels}} T_{a,x}^{(t)} \left[ \ln\tau_a - 1\frac{\ln(2\pi\sigma_a^2)}{2} - \frac{(I(x) - \mu_a)^2}{2\sigma_a^2} \right]$$

$$\tau^{(t+1)} = \underset{\tau}{\operatorname{argmax}} \left\{ \sum_{a=1}^{N_{analytes}} \left( \left[ \sum_{x=1}^{N_{pixels}} T_{a,x}^{(t)} \right] \ln\tau_a \right) \right\}$$

$$\tau_j^{(t+1)} = \frac{1}{N_{pixels}} \sum_{x=1}^{N_{pixels}} T_{j,x}^{(t)}$$

$$(\mu_j^{(t+1)}, \sigma_j^{(t+1)}) = \underset{\mu,\sigma}{\operatorname{argmax}} \left\{ \sum_{a=1}^{N_{analytes}} \left( \left[ \sum_{x=1}^{N_{pixels}} T_{a,x}^{(t)} \right] \left[ -1\frac{\ln(2\pi\sigma_a^2)}{2} - \frac{(I(x) - \mu_a)^2}{2\sigma_a^2} \right] \right) \right\}$$

$$\mu_j^{(t+1)} = \frac{\sum_{x=1}^{N_{pixels}} T_{j,I(x)}^{(t)} I(x)}{\sum_{x=1}^{N_{pixels}} T_{j,I(x)}^{(t)}}$$

$$\sigma_j^{(t+1)} = \frac{\sum_{x=1}^{N_{pixels}} T_{j,I(x)}^{(t)} (I(x) - \mu_j^{(t+1)})^2}{\sum_{x=1}^{N_{pixels}} T_{j,I(x)}^{(t)}}$$

The main problem with this simple model is that it doesn't code any higher order structure to the pixels. There is no prior probability associated with more realistic arrangements of pixels. Only tau determines the proportion of analyte classes. Thus, once can use the tau variable to insert in the blob prior probability model, in particular at the step of updating membership probabilities.

Thus a modified Bayesisan inference procedure may be applied with a much more sophisticated Bayesian prior. In the basic EM implementation, there is no real prior distribution. The variable tau represents the a priori relative proportion of each class but even this variable is unspecified and estimated during the inference procedure. Thus, there is no a priori belief about the distribution of classes in the basic EM model. In our model, the model prior is represented by the multi-scale analyte model. Tau becomes a function of position (and other variables), not just a global proportion.

$$L(\theta; I, A) = f(I, A \mid \theta)$$

$$= f(A) f(I \mid A, \theta)$$

$$= f(A) \prod_{x=1}^{N_{pixels}} G(I(x); \mu_{A(x)}, \sigma_{A(x)})$$

$$= f(A) \exp\left\{ \sum_{x=1}^{N_{pixels}} -\frac{\ln(2\pi\sigma_a^2)}{2} - \frac{(I(x) - \mu_a)^2}{2\sigma_a^2} \right\}$$

$$Q(\theta \mid \theta^{(t)}) = E[\ln L(\theta; I, A)]$$

$$= E\left[ \ln f(A) + \sum_{x=1}^{N_{pixels}} -\frac{\ln(2\pi\sigma_a^2)}{2} - \frac{(I(x) - \mu_a)^2}{2\sigma_a^2} \right]$$

$$= E[\ln f(A)] + \sum_{a=1}^{N_{analytes}} \sum_{x=1}^{N_{pixels}} T_{a,x}^{(t)} \left[ -1\frac{\ln(2\pi\sigma_a^2)}{2} - \frac{(I(x) - \mu_a)^2}{2\sigma_a^2} \right]$$

$$(\mu_j^{(t+1)}, \sigma_j^{(t+1)}) = \underset{\mu,\sigma}{\operatorname{argmax}} \left\{ \sum_{a=1}^{N_{analytes}} \left( \left[ \sum_{x=1}^{N_{pixels}} T_{a,x}^{(t)} \right] \left[ -1\frac{\ln(2\pi\sigma_a^2)}{2} - \frac{(I(x) - \mu_a)^2}{2\sigma_a^2} \right] \right) \right\}$$

$$\mu_j^{(t+1)} = \frac{\sum_{x=1}^{N_{pixels}} T_{j,I(x)}^{(t)} I(x)}{\sum_{x=1}^{N_{pixels}} T_{j,I(x)}^{(t)}}$$

$$\sigma_j^{(t+1)} = \frac{\sum_{x=1}^{N_{pixels}} T_{j,I(x)}^{(t)} (I(x) - \mu_j^{(t+1)})^2}{\sum_{x=1}^{N_{pixels}} T_{j,I(x)}^{(t)}}$$

The membership probability function is defined as follows:

$$f(I, A \mid \theta) = f(A) f(I \mid A, \theta) = f(A) \sum_{x=1}^{N_{pixels}} G(I(x); \mu_{A(x)}, \sigma_{A(x)})$$

$$f(A \mid I, \theta) = \frac{1}{Z} f(A) f(I \mid A, \theta)$$

$$P(A(x) = j \mid I(x) = i, \theta) = \frac{1}{Z} P(A(x) = j) f(I(x) = i \mid A(x) = j, \theta)$$

$$T_{j,x}^{(t)} := P(A(x)^{(t)} = j \mid I(x) = i, \theta)$$

$$T_{j,x}^{(t)} := \frac{P(A(x)^{(t)} = j) G(I(x); \mu_j^{(t)}, \sigma_j^{(t)})}{\sum_{a=1}^{N_{analytes}} P(A(x)^{(t)} = a) G(I(x); \mu_a^{(t)}, \sigma_a^{(t)})}$$

(membership probabilities)

-continued $$
\begin{aligned}
T_{j,x}^{(t)} &:= \frac{1}{Z} \underset{models}{E}[P(A(x) = j)P(I(x) = i \mid A(x) = j, \theta)] \\
&:= \frac{1}{Z} \sum_{\alpha \in models} P(A = \alpha)P(A(x) = j)P(I(x) = i \mid A(x) = j, \theta) \\
&:= \frac{1}{Z} \sum_{\alpha \in models} P(N) \prod f(C_c) \prod f(B_b) P(A(x) = j) \\
&\quad P(I(x) = i \mid A(x) = j, \theta)
\end{aligned}
$$

The inference algorithm is as follows. At each step of iteration, the membership probability map is initialized to zero so that all classes have zero probability. Then for all possible model configurations, the membership probability map may be added to as follows:

$$T_{j,x}{}^{(t)} += P(N^{(t)}) \Pi f(C_c{}^{(t)} \Pi f(B_b{}^{(t)}) P(A(x)^{(t)}=j) P(I(x)=i \mid A(x)^{(t)}=j,\theta)$$

Finally, the probability vector may be normalized at each pixel in the membership probability map to restore the completeness assumption. Advantageously one can iterate over all model configurations. This is done by sequentially considering values for N from 0 to a relatively low value, for instance 9, at which point extremely few sections have ever been observed to have as many blobs. For each value of N one can examine different putative blob configurations. The putative blobs may be thresholded to a small number (N) based on their individual blob probabilities. Then, all of the permutations of N blobs are considered. Thus, one can simultaneously considering all of the most likely blob configurations and weighting each model by its prior probability. This procedure is obviously an approximate inference scheme since the full space of multi-scale model configurations may not be considered. One can assume, however, that by considering the most likely (in terms of both N and blobs), a good approximation is achieved. This procedure also assumes that the weighted average of the most likely configurations provides a good estimate at each individual pixel. Another alternative is to perform a constrained search of model configurations and select the highest likelihood model as the MAP (maximium a posteriori) estimate.

Further exemplary statistical models (e.g., the posterior P(A\I)) are also described herein. In a CT angiography the following information may be available:

- Intensity
  - CT Hounsfield units or MR intensities
  - Possibly other imaging features
- Position relative to anatomy
  - Where in the plaque a pixel is
- Neighboring pixels
  - E.g., for smoothing contours through level sets Posterior probability may be computed as:

$$P(A \mid I) \propto P(I \mid A) \cdot P(A)$$

Thus, the following image information may influences analyte probability, Ai(x)

- I(x) is observed image intensity (possibly a vector)
- T(x) is observed relative wall thickness from image segmentation
- F(x) are CT image features
- S(x) are features of vessel wall shape (e.g., luminal bulge)

In some embodiments a Metropolis-Hastings like approach may be utilized. In other embodiments a maximum a posteriori approach may be applied.

The following are example algorithmic possibility for a statistical analysis model. In some embodiments, the model may utilize Belief propagation (AKA max sum, max product, sum product messaging). Thus, for example a Viterbi (HMM) type approach may be utilized, e.g., wherein, hidden states are the analyte assignments, A, Observed states are the image intensities, I. This approach may advantageously find a MAP estimate may be argmax P (A|I). In some embodiments a soft output Viterbi algorithm (SOVA) may be utilized. Note that reliability of each decision may be indicated by difference between chosen (survivor) path and discarded path. Thus, this could indicate reliability of each pixel analyte classification. In further example embodiments a forward/backward Baum-Welch (HMM) approach may be utilized. For example one can compute most likely state at any point in time but not the most likely sequence (see Viterbi).

Another possible technique is the Metropolis-Hastings (MCMC) approach, e.g., wherein one repeatedly samples A and weights by likelihood and prior. In some embodiments, a simple MRF version for sampling may be utilized. Note that it may be particularly advantageous to sample the posterior directly. In example embodiments, one can build up per-pixel histograms of analyte class.

Other algorithm possibilities include applying a Gibbs Sampler, Variational Bayes (similar to EM), Mean field approximation, a Kalman filter, or other techniques.

As noted above, in some embodiments an Expectation Maximization (EM) posterior approach may be utilized. Under this approach, observed data X is the imaging values, unknown parameters θ are due to the analyte map (but not including analyte probabilities) and latent variable Z is the analyte probability vector. One key feature of this approach is that it enables iterating between estimating class membership (Z) and model parameters (θ) since they each depend on each other. However, since the analyte map separates out analyte probabilities, the approach may be modified such that the current class membership doesn't have to influence the model parameters (since these are learned this during a training step). Thus, EM basically learning the model parameters as it iterates through the current data. Advantageously, exemplary implementation of the EM approach iteratively compute maximum likelihood but assumes a flat prior.

Techniques are also provided herein for representing longitudinal covariance. Due to wide spacing of histology slices (e.g., 4 mm), sampling may not faithfully capture the longitudinal variation in analytes. However, 3D image analysis is typically performed and presumably there is some true longitudinal covariance. The problem is that histological information typically isn't provided for longitudinal covariance. Nonetheless the exemplary statistical models disclosed herein may reflect a slow variation in longitudinal direction.

Figure 15:
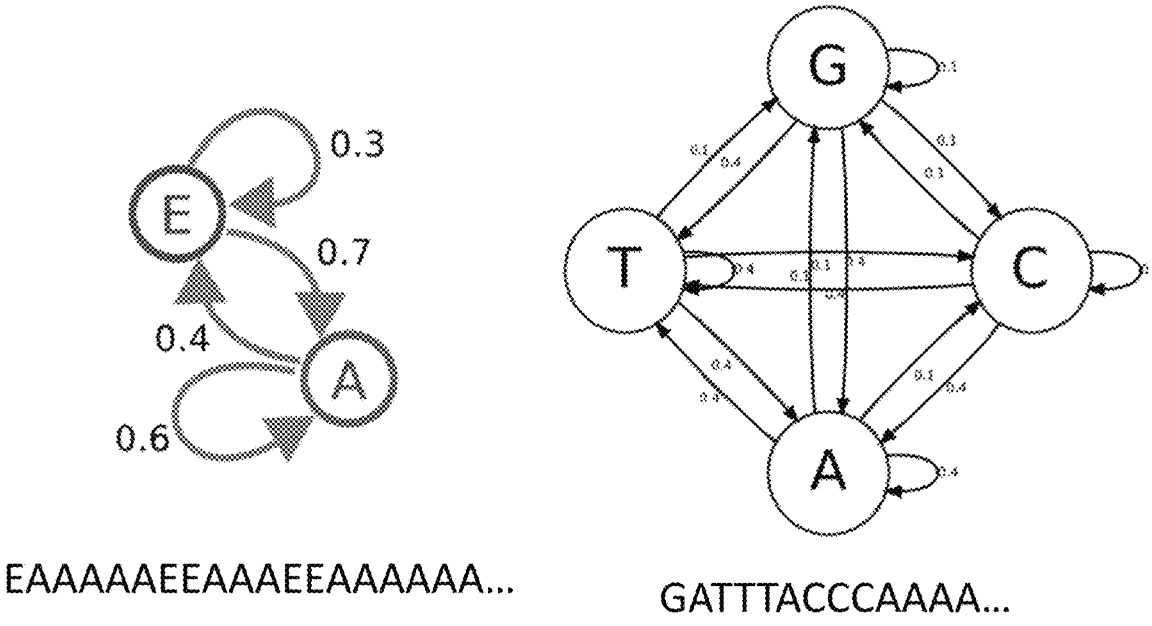
FIG. 15 depicts exemplary implantation of a 1D Markov chain, according to the present disclosure.
Figure 16:
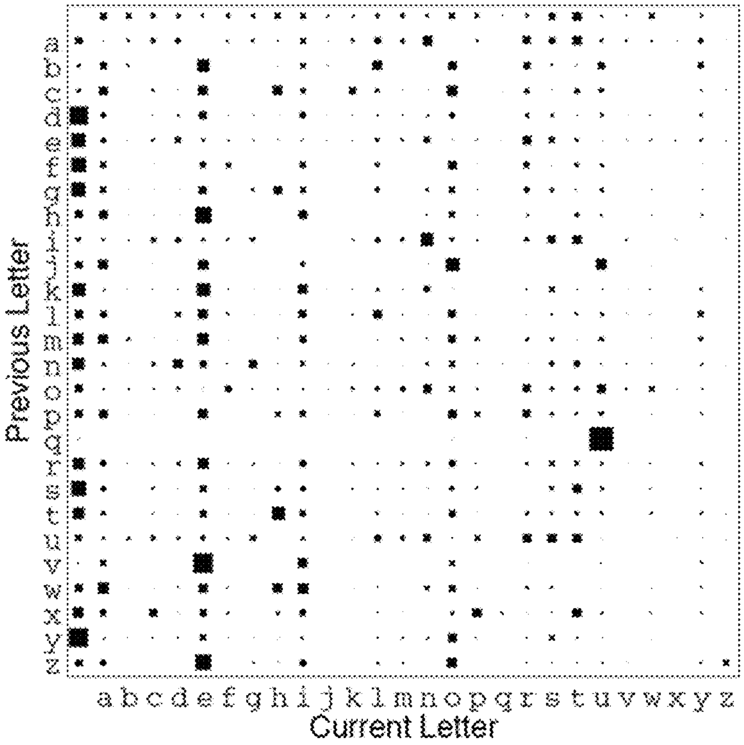
FIG. 16 depicts an example first order Markov chain for a text probability table, according to the present disclosure.

In some embodiments, a Markov model/chain may be applied. FIG. 15 depicts exemplary implantation of a 1D Markov chain for Text/DNA. Conventionally, when applied to images in MRF Markov chains are typical as low order as possible. A higher order chain may be advantageous, however, due to conditional independence (Markov property). Otherwise the data may be too scrambled to be of value. This is demonstrated by the 1D sampling of an exemplary Markov chain as applied to text:

Uniform probability sampling output:

earryjnv anr jakroyvnbqkrxtgashqtzifzstqaqwgktlfgidmxxaxmmhzmgbya mjgxnlyattvc rwpsszwfhimovkvgknlgddou nmytnxpvdescbg k syfdhwqdrj jmcovoyodzkcofmlycehpcqpuflje xkcykcwbdaifculiluyqerxfwlmpvtlyqkv 0-order Markov chain output:

ooyusdii eltgotoroo tih ohnnatti gyagditghreay nm roefnnasos r naa euuecocrrfca ayas el s yba anoropnn laeo piileo hssiod idlif beeghec ebnniioouhuehinely neiis cnitcwasohs ooglpyocp h trog l $1^{st}$ order Markov chain output:

icke inginatenc blof ade and jalorghe y at helmin by hem owery fa st sin r d n cke s t w anks hinioro e orin en s ar whes ore jot j whede chrve blan ted sesoure-thegebe inaberens s ichath fle watt o $2^{nd}$ order Markov chain output:

he ton th a s my caroodif flows an the er ity thayertione wil ha m othenre re creara quichow mushing whe so mosing bloack abeenem used she sighembs inglis day p wer wharon the graiddid wor thad k $3^{rd}$ order Markov chain output:

es in angull o shoppinjust stees ther a kercourats allech is hote ternal liked be weavy because in coy mrs hand room him rolio und ceran in that he mound a dishine when what to bitcho way forgot p FIG. 16 depicts an example first order Markov chain for a text probability table. Note that such tables are exponentially sized in terms of order:

D=order of Markov chain

N=number of letters

Size=$N^D$

Thus, higher order leads to problems with dimensionality. Advantageously histology samples have a very high resolution. However, since histology samples are not statistically independent, this may lead to overfitting as later described in greater detail. In general, the more conditional dependence that is modeled, the more predictive the model can be.

Figure 17:
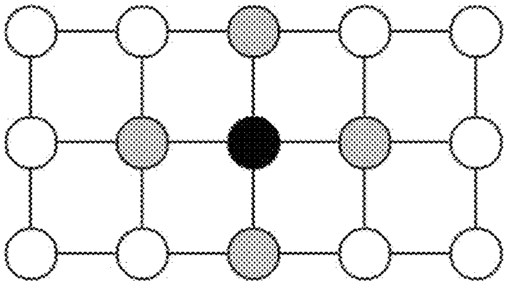
FIG. 17 depicts conditional dependence of a first pixel based on its neighboring pixels, according to the present disclosure.

In example embodiments, a 2D Markov random field (MRF) may be used for pixel values instead of a 1D sequence such as for letters. FIG. 17 depicts conditional dependence of a first pixel (black) based on its neighboring pixels (gray). In example embodiments cliques may make use symmetry to reduce the number of dependencies in half. In some embodiments, the values of pixels could be simple image intensities or could be probability values for classification problems. Problems exist with typical MRF use. Conventional MRF almost always is limited to the nearest neighbor pixels providing conditional dependence which greatly reduces the specificity of the probability space represented; usually just black/white blobs for very general purpose segmentation/filtering; extremely short range dependencies. However, whereas pixels are highly discretized a blob just missing one pixel and falling in the next may completely change the probability distribution. Thus a real image structure is much more continuous than is typically accounted for using MRF.

For this reasons the systems and methods of the present disclosure may advantageously utilize an inference procedure, e.g., a Bayes type rule of Posterior α Likelihood×Prior (P(A/I) α P(I/A)×P(A)). Using a crossword type analogy, the inference procedure implemented by the systems and methods of the subject application is a bit like trying to OCR a crossword puzzle from a noisy scan. Knowledge (even imperfect knowledge of several squares may help inform an unknown square in the crossword puzzle. Efficiently is improved even more by considering both vertical and horizontal direction simultaneously. In example embodiments, the inference procedure may be heuristic. For example, one can initialize with uninformed prior, then, solve the easier ones first, which gives you clues about the harder ones which are solved later. Thus easy to detect biological properties such as calcium may inform the existence of other harder to detect analytes such as lipids. Each step of the inference procedure may narrow the probability distributions for unsolved pixels.

As noted above a high order Markov chain is preferable to obtain usable data. The disadvantage of utilizing a higher order Markov approach is that there may not be enough data to inform the inference process. In example embodiments, this issue may be addressed by utilizing density estimation methods such as Parzen windowing or utilizing kriging techniques.

To form an inference procedure one may initialize with unconditional prior probabilities of analytes and then use a highest level of evidence to start narrowing down probabilities. For example in some embodiments, an uncertain width may be associate with each analyte probability estimate. In other embodiments, closeness to 1/N may represent such uncertainty.

Notably, the term "Markov" is used loosely herein since the proposed Markov implementations are not memoryless but rather are explicitly trying to model long range (spatial) dependencies.

Because the CT resolution is low compared to histology and plaque anatomy, in some embodiments it may be preferable to utilize a continuous space (time) Markov model rather than discrete space (time). This may work well with the level set representation of probability maps since they naturally work well with sub-pixel interpolation. Discrete analyte states makes the model a discrete space model. However, if one represents continuous probabilities rather than analyte presence/absence, then it becomes a continuous space model.

Turning to lung based applications, table 4 below depicts exemplary biological properties/analytes which may utilized with respect to a hierarchical analytics framework for such applications.

TABLE 5

Biologically-objective measurands Supported by lung based applications

| Category | Description | Readings | Units/Categories |
| --- | --- | --- | --- |
| Size | The size of the lesion | Volume (lesion, solid portion, ground-glass portion) | mm^3 |
| | | Longest diameter and perpendicular (lesion, solid portion, ground-glass portion) | mm |

TABLE 5-continued

| Biologically-objective measurands Supported by lung based applications | | | |
|---|---|---|---|
| Category | Description | Readings | Units/Categories |
| Shape/ Margin | Overall shape of the lesion and descriptions of its border which may indicate certain cancers or diseases (possibly including fibrotic scarring) | Shape | sphericity (unitless: round = 1, oval ~0.5, line = 0)/lobulated-irregular/cavitary, speculation, notch/cut |
| | | Margin | Tumor margin scale (HU) Tumor margin window (HU/mm) |
| | | Topology | Euler Number |
| Solidity | Mean development of cell types or lack thereof that make up the lesion (differentiation, organization) | Volume % solid of Lesion (C/T ratio) | % |
| | | Volume % ground-glass of Lesion | % |
| | | Solid density | g/ml |
| | | Ground glass density | g/ml |
| | | Mass of solid | g |
| | | Mass of ground glass | g |
| Heterogeneity | Covariance and development of cell types or lack thereof that make up the lesion (differentiation, organization) | SD (variation of solid density) | g/ml |
| | | SD (variation of ground glass) | g/ml |
| | | Pattern | Nonsolid or ground-glass opacity (pure GGN)/ perifissural/part-solid (mixed GGN)/solid |
| | | Solid portion pattern | Radial intensity distribution $1^{st}$ and $2^{nd}$ order statistics (Central/ central with ring/diffuse/ peripheral) |
| | | Spatial coherence (texture, "clumpiness", localized heterogeneity) | NSM (non-spatial methods); SGLM (apatial gray-level methods) e.g., Haralick; fractal analysis (FA): Lacunarity, average local variance, variance of local variance, average of local average; filters & transfroms (F&T) e.g., Gabor |
| Invasive Potential | Measure of Lesion's invasive extent or potential extent | Pleural contact length (AKA arch distance) | mm |
| | | Pleural contact length-to-maximum lesion diameter | unitless |
| | | Pleural Involvement | Displacement from expected location |
| | | Lobe Location | Upper/middle/lower lobe//right/left |
| | | Lobe centrality | unitless (1 = lobe center, 0 = lobe boundary) |
| | | Airway Involvement/air bronchogram | category |
| | | Vascular changes | Dilated/rigid/convergent/ tortuous |
| Calcification | Response to injurious agent (dystrophic) or caused by deranged metabolism (metastatic) | Volume | mm^3 |
| | | Volume % of Lesion | % |
| | | Distribution | Central/peripheral/ diffuse |
| | | Pattern | amorphous/punctuate/ reticular/popcorn/ laminated |
| Cell Metabolism | Measures of cell metabolism | Uptake | SUV (unitless), % ID/g |
| | | Glycolytc volume | |
| <each non-categorical measurand above> | Change assessed between as few as 2 but arbitrarily many timepoints | Pairwise arithmetic difference | In units of measurand |
| | | Pairwise ratio | unitless |
| | | Pairwise doubling time | days/weeks/months |
| | | Polynomial fit coefficients | |
| | | Non-arithmetic change assessment with registration, e.g., vascular changes | |

TABLE 5-continued

Biologically-objective measurands Supported by lung based applications

| Category | Description | Readings | Units/Categories |
| --- | --- | --- | --- |
| <each non-categorical measurand above> | Assessed over multiple targets according to response criteria, e.g., RECIST, WHO, etc. | Total Tumor Burden | mm^3 |
| | | Tumor Number | unitless |
| | | Multilobar | True/false |
| | | Lymph Node status | category |
| | | Metastasis | category |
| | | Response | category |

In particular, systems may be configured to detect lung lesions. Thus, an exemplary system may be configured for whole lung segmentation. In some embodiments, this may involve use of minimum curvature evolution to solve juxtapleural lesion problems. In some embodiments, the system may implement lung component analysis (vessel, fissure, bronchi, lesion etc.). Advantageously a Hessian filter may be utilized to facilitate lung component analysis. In some embodiments lung component analysis may further include pleural involvement, e.g., as a function of fissure geometry. In further embodiments, attachment to anatomic structures may also be considered. In addition to lung component analysis, separate analysis of ground glass vs. solid stated may also be applied. This may include determination of geometric features, such as volume, diameter, sphericity, image features, such as density and mass, and fractal analysis.

Fractal analysis may be used to infer lepidic growth patterns. In order to perform fractal analysis on very small regions of interest, our method adaptively modifies the support for convolution kernels to limit them to the region of interest (i.e., lung nodule). Intersecting vessels/bronchi as well as non-lesion feature may be masked out for the purposes of fractal analysis. This is done by applying IIR Gaussian filters over masked local neighborhoods and normalizing with IIR blurred binary masking. In some embodiments, fractal analysis may further include determining lacunarity (based on variance of the local mean). This may be applied with respect to lung lesions, subparts of lesions. In example embodiments, IIR Gaussian filters or circular neighborhoods may be applied. In some embodiments IIR may be utilized to compute variance. Average of local variance (AVL) may also be computed, e.g., as applied to lung lesions. Likewise, a variance of local variance may be calculated.

In example embodiments, both lesion structure and composition may be calculated. Advantageously calculating lesion structure may utilize full volumetry of this sections thereby improving on calculating size measurement change. Measurements such as sub-solid and ground glass opacity (GGO) volume may also be determined as part of assessing lesion structure. Turning to lesion composition, tissue characteristics such as consolidation, invasion, proximity and perfusion may be calculated e.g., thereby reducing false positive rate relative to conventional analytics.

Figure 18:
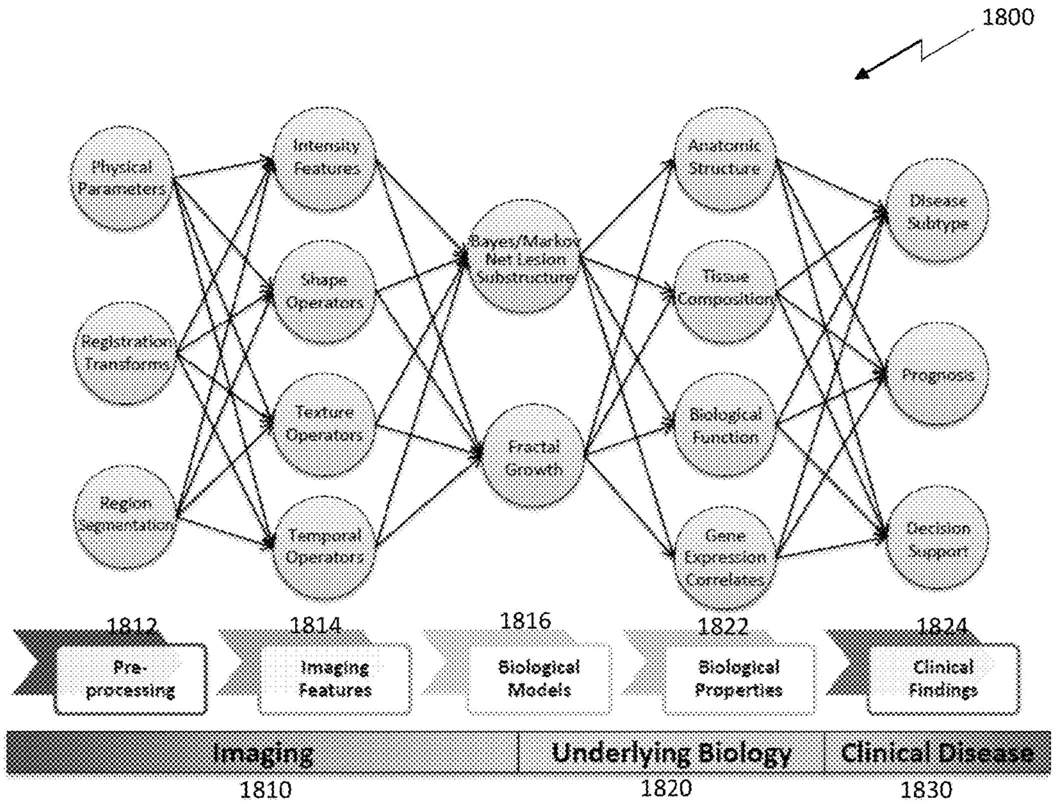
FIG. 18 depicts a further exemplary hierarchical analytics framework according to the present disclosure.

With reference now to FIG. 18, a further exemplary hierarchical analytics framework 1800 for the systems of the present disclosure is depicted. FIG. 18 may be understood as an elaboration of FIG. 1 elucidating greater detail with respect to exemplary intermediate processing layers of the hierarchical inference system. Advantageously the hierarchical inferences still flow from imaging data 1810 to underlying biological information 1820 to clinical disease 1800. Notably, however, the framework 1800 includes multiple levels of data points for processing imaging data in order to determine biological properties/analytes. At a preprocessing level 1812, physical parameters, registrations transformations and region segmentations may be determined. This preprocessed imaging information may then be utilized to extract imaging features at the next level of data points 1814 such as intensity features, shape, texture, temporal characteristics, and the like. Extracted image features may next utilized at level 1816 to fit one or more biological models to the imaged anatomy. Example models may include a Bayes/Markov net lesion substructure, a fractal growth model, or other models such as described herein. The biological model may advantageously act as a bridge for correlating imaging features to underlying biological properties/analytes at level 1822. Example biological properties/analytes include anatomic structure, tissue composition, biological function, gene expression correlates, and the like. Finally, at level 1832 the biological properties/analytes may be utilized to determine clinical findings related to the pathology including, e.g., related to disease subtype, prognosis, decision support and the like.

The invention claimed is:

1. A system comprising a processor and a non-transient storage medium including processor executable instructions implementing an analyzer module including a hierarchical analytics framework configured to:

utilize a first set of machine learned algorithms to identify and quantify a set of biological properties utilizing medical imaging data; and utilize a second set of machine learned algorithms independent from the first machine learned algorithm to identify and characterize one or more medical conditions based on the quantified biological properties, wherein the characterization of the one or more medical conditions is indicative of therapeutic/treatment options or further diagnostics;

wherein the algorithms in each of the first and second sets of algorithms are independently derived utilizing machine learning; and wherein the first set of algorithms is distinctly trained from the second set of algorithms.

2. The system of claim 1, wherein the analytics framework implements an algorithm for identifying and characterizing the one or more medical conditions based on the quantified biological properties wherein a training set from one or more non-radiological or non-imaging data sources was used in training the algorithm.

3. The system of claim 1, wherein the analytics framework implements an algorithm for identifying and quantifying the biological properties utilizing radiological imaging data, wherein a training set from one or more non-radiological data sources was used training the algorithm.

4. The system of claim 1, wherein data from a plurality of same or different types of data sources is incorporated into the process of identifying and characterizing the one or more medical conditions.

5. The system of claim 4, wherein data from one or more non-imaging data sources is used in conjunction with the imaging data such that the set of biological properties includes one or more biological properties identified or quantified based at least in part on the data from one or more non-imaging data sources.

6. The system of claim 5, wherein the data from non-imaging sources includes one or more of (i) demographics, (ii) results from cultures or other lab tests, (iii) genomic, proteomic or metabolomic expression profiles, or (iv) diagnostic observations.

7. The system of claim 4, wherein data from one or more non-radiological data sources is used in conjunction with radiological imaging data such that the set of biological properties includes one or more biological properties identified or quantified based at least in part on the data from one or more non-radiological data sources.

8. The system of claim 1, wherein the system is configured to simultaneously provide a user with information on the one or more medical conditions as well as the underlying biological properties used in the identification or characterization of the one or more medical conditions.

9. The system of claim 1, wherein the system is configured to determine at least one of (i) which of the biological parameters in the set have the greatest amount of uncertainty regarding the identification or quantification thereof or (ii) which of the biological parameters in the set are most deterministic of the identification or characterization of the one or more medical conditions.

10. The system of claim 1, wherein the identifying and quantifying the set of biological properties utilizing the imaging data includes receiving patient data including the image data and parsing the received data into a set of empirical parameters including one or more imaging features of an imaged target.

11. The system of claim 10, wherein the parsing the received data includes pre-processing image data including performing one or more of: (i) intensity vector analysis, (ii) image registration and transformation analysis or (iii) anatomic region analysis.

12. The system of claim 10, wherein the imaging features are derived based on one or more of: (i) temporal operators, (ii) fractal analysis, (iii) spatial operators or (iv) or an augmented Markov analysis.

13. The system of claim 1, wherein an imaged target is a lesion and wherein the biological properties include (i) a size of the lesion, (ii) a shape of the lesion, (iii) a characterization of the margin of the lesion, (iv) a solidity of the lesion, (v) a heterogeneity of the lesion, (vi) a measure of the lesion's invasive extent or potential extent, (vii) a compositional measure of calcification related to the lesion and (viii) a measure of cell metabolism with respect to the lesion.

14. The system of claim 1, wherein at least one or the biological properties is quantified by assessing differences between a plurality of targets.

15. The system of claim 1, wherein an imaged target is a blood vessel and wherein the biological properties include (i) an indication of plaque coverage of the vessel wall, (ii) an indication of stenosis of the vessel wall, (iii) an indication of dilation of the vessel wall, and (iv) an indication of vessel wall thickness.

16. The system of claim 1, wherein an imaged target is a vascular tissue and wherein the biological properties include (i) an indication of a lipid core of the vascular or related tissue, (ii) a measure of fibrosis of the vascular or related tissue, (iii) a measure of calcification of the vascular or related tissue, (iv) an indication of any hemorrhage in the vascular or related tissue, (v) a measure of permeability of the vascular or related tissue, (vi) an indication of thrombosis of the vascular or related tissue, and (vii) an indication of ulceration of the vascular or related tissue.

17. The system of claim 1, wherein set of biological properties includes one or more anatomical, morphological, structural, compositional, functional, chemical, biochemical, physiological, histological or genetic characteristics.

18. The system of claim 1, wherein the characterization of the one or more medical conditions includes phenotyping the medical conditions.

19. The system of claim 18, wherein the characterization of the one or more medical conditions further includes determining predictive outcomes for the medical conditions.

20. The system of claim 19, wherein the one or more predictive outcomes are predicated on a predetermined causality rating between phenotypes and the predictive outcomes.

21. The system of claim 1, wherein the storage medium further includes processor executable instructions implementing a trainer module, for training one or more algorithms implemented by the hierarchical analytics framework.

22. The system of claim 1, wherein the storage medium further includes processor executable instructions implementing a cohort module for enabling a user to define one or more cohort groupings of individuals for further analysis.

23. The system of claim 1, wherein the analyzer module includes algorithms for calculating imaging features from the imaging data, wherein some of the imaging features are computed on a per-pixel basis, while other imaging features are computed on a region-of-interest basis.

24. The system of claim 1, wherein the algorithms in each of the first and second sets of algorithms are independently characterized by one or more of neural nets, SVMs, partial least squares, principle components analysis or random forests.

25. The system of claim 1, wherein the analyzer module is configured to enable delineating of a field for the imaging data.

26. The system of claim 25, wherein the delineating the field includes segmenting one of organs, vessels, lesion or other application-specific anatomical features.

27. The system of claim 25, wherein the field is a cross-sectional slice of a blood vessel.

28. The system of claim 26, wherein the analyzer module is further configured to delineate a target in the field and determining anatomic structure or composition characteristics for the target, wherein the target is a blob in the cross-sectional slice of a blood vessel.

29. The system of claim 1, wherein the hierarchical analytics framework includes fitting a biological model utilizing the imaging data wherein the biological model is then utilized to identify and quantify the biological properties.

30. The system of claim 29, wherein the model is a fractal model.

31. The system of claim 29, wherein the model is based on hybrid Bayesian/Markovian network.

32. The system of claim 29, wherein the model computes biological parameters for one or more contiguous regions of a given analyte type.

33. The system of claim 32, wherein the model further computes biological parameters based on relationships between two-or more different contiguous regions of a given analyte type or given analyte types.

34. The system of claim 33, wherein the model further computed biological parameters based on a number of contiguous regions of a given analyte type or given analyte types.

35. The system of claim 29, wherein the model employs expectation maximization which accounts for conditional dependence between pixels.

36. A system comprising a processor and a non-transient storage medium including processor executable instructions implementing an analyzer module including a hierarchical analytics framework configured to:

utilize a first set of algorithms to identify and quantify a set of biological properties utilizing medical imaging data; and utilize a second set of algorithms to identify and characterize one or more medical conditions based on the quantified biological properties, wherein the characterization of the one or more medical conditions is indicative of therapeutic/treatment options or further diagnostics, wherein information relating to the set of identified and quantified biological properties is adjusted after an initial identification or quantification thereof based on contextual information which adjusts or updates one or more probabilities impacting the identification or quantification of at least one of the biological properties in the set.

37. The system of claim 36, wherein the contextual information includes at least one of patient demographics, correlations relating different biological properties, or correlations relating one or more of the identified medical conditions to one or more biological properties.

38. A system comprising a processor and a non-transient storage medium including processor executable instructions implementing an analyzer module including a hierarchical analytics framework configured to:

utilize a first set of algorithms to identify and quantify a set of biological properties utilizing medical imaging data; and utilize a second set of algorithms to identify and characterize one or more medical conditions based on the quantified biological properties, wherein the characterization of the one or more medical conditions is indicative of therapeutic/treatment options or further diagnostics, wherein information relating to the identified and characterized one or more medical conditions is adjusted after an initial identification or characterization thereof based on contextual information which adjusts or updates one or more probabilities impacting the identification or characterization of at least one of one or more medical conditions.

39. A non-transient storage medium including processor executable instructions for:

receiving patient data including a set of empirical parameters, the set of empirical parameters including one or more imaging features of an imaged target;

utilizing a first algorithm to identify and quantify one or more logical characteristics indicated by the empirical parameters, the logical characteristics representing pathological features;

identifying a set of pathological features, the set of pathological features including the one or more quantified logical characteristics; and utilizing a second algorithm to identify one or more pathologies indicated by the set of pathological features, wherein the one or more pathologies are indicative of therapeutic/treatment options or further diagnostics;

wherein the first algorithm includes a scoring algorithm for determining a confidence weighting for each of the logical characteristic;

wherein the confidence weighting for each logical characteristic includes a confidence weighting for a quantification of that logical characteristic; and wherein the confidence weighting for the quantification of the logical characteristic is determined according to a probability distribution across a range of values for the logical characteristic.

40. The non-transient storage medium of claim 39 wherein a confidence threshold is utilized to identify the logical characteristics indicated by the empirical parameters.

41. The non-transient storage medium of claim 39 wherein the first algorithm is derived utilizing a training collection of a plurality of sets of empirical parameters each with associated with known quantifications of one or more pathological features.

42. The non-transient storage medium of claim 39 wherein the second algorithm includes a scoring algorithm for determining a confidence weighting for each of the pathologies.

43. The non-transient storage medium of claim 42 wherein the confidence weighting for each pathology includes a confidence weighting for a phenotype thereof.

44. The non-transient storage medium of claim 42 wherein a confidence threshold is utilized to identify the pathologies indicated by the pathological features.

45. The non-transient storage medium of claim 39 wherein the first and second algorithms are each derived independently utilizing machine learning.

46. The non-transient storage medium of claim 39 wherein the first and second algorithms are each independently characterized by one or more of machine learning, decision trees, differential equations, polynomial expressions, pattern matching or parsing, dynamic programming, or state space searches.

47. A non-transient storage medium including processor executable instructions for:

receiving patient data including a set of empirical parameters, the set of empirical parameters including one or more imaging features of an imaged target;

utilizing a first algorithm to identify and quantify one or more logical characteristics indicated by the empirical parameters, the logical characteristics representing pathological features;

identifying a set of pathological features, the set of pathological features including the one or more quantified logical characteristics; and utilizing a second algorithm to identify one or more pathologies indicated by the set of pathological features, wherein the one or more pathologies are indicative of therapeutic/treatment options or further diagnostics;

wherein the second algorithm includes a scoring algorithm for determining a confidence weighting for each of the pathologies;

wherein the confidence weighting for each pathology includes a confidence weighting for a phenotype thereof; and wherein the confidence weighting for the phenotype is determined according to a probability distribution across a range of phenotypes for the pathology.

48. A non-transient storage medium including processor executable instructions for:

receiving patient data including a set of empirical parameters, the set of empirical parameters including one or more imaging features of an imaged target;

utilizing a first algorithm to identify and quantify one or more logical characteristics indicated by the empirical parameters, the logical characteristics representing pathological features;

identifying a set of pathological features, the set of pathological features including the one or more quantified logical characteristics; and utilizing a second algorithm to identify one or more pathologies indicated by the set of pathological features, wherein the one or more pathologies are indicative of therapeutic/treatment options or further diagnostics, wherein the second algorithm includes a scoring algorithm for determining a confidence weighting for each of the pathologies, and wherein an initial confidence weighting in a first pathology is used to adjust an initial confidence weighting in a second related pathology.

49. The non-transient storage medium of claim 48 wherein an initial confidence weighting in the first pathology is used to adjust an initial confidence weighting in a logical characteristic and wherein the adjusted confidence weighting in the logical characteristic is used to indicate the second related pathology.

50. A system comprising:

an imaging device for imaging a target;

a processor configured for: (i) receiving patient data including a set of empirical parameters, the set of empirical parameters including one or more imaging features of the imaged target; (ii) utilizing a first machine learned algorithm to identify and quantify one or more logical characteristics indicated by the empirical parameters, the logical characteristics representing pathological features; (iii) identifying a set of pathological features, the set of pathological features including the one or more quantified logical characteristics; and (iv) utilizing a second machine learned algorithm independent from the first machine learned algorithm to identify one or more pathologies indicated by the set of pathological features; and a user interface for outputting information relating to the one or more identified pathologies, wherein the one or more pathologies are indicative of therapeutic/treatment options or further diagnostics;

wherein the first and second algorithms are independently derived utilizing machine learning; and wherein the first algorithm is distinctly trained from the second set of algorithm.

51. The system of claim 50 wherein the identifying the one or more pathologies includes identifying a phenotype for each pathology.

52. The system of claim 50 wherein the one or more logical characteristics include one or more morphological, developmental, biochemical or physiological characteristics of the imaged target.

53. The system of claim 50 wherein the first algorithm includes a scoring algorithm for determining a confidence weighting for each of the logical characteristics.

54. The system of claim 53 wherein the confidence weighting for each logical characteristic includes a confidence weighting for a quantification of that logical characteristic.

55. The system of claim 54 wherein the confidence weighting for the quantification of the logical characteristic is determined according to a probability distribution across a range of values for the logical characteristic.

56. The system of claim 50 wherein the set of empirical parameters further includes one or more of: (i) demographics, (ii) results from cultures or other lab tests, (iii) genomic, proteomic or metabolomic expression profiles, or (iv) diagnostic observations.

57. The system of claim 50 wherein the logical characteristics include values for quantitative biological analytes.

58. The system of claim 50 wherein the first and second algorithms are characterized by one or more of neural nets, SVMs, partial least squares, principle components analysis, random forests.

59. The system of claim 50 wherein the first and second algorithms are trained utilizing one or more of empirical data or expert opinion.

60. The system of claim 50 further including processor executable instructions for determining one or more predictive outcomes for the identified pathologies.

61. The system of claim 60 wherein the one or more predictive outcomes for the identified pathologies are determined based on identifying a phenotype for each pathology.

62. The system of claim 61 wherein the one or more predictive outcomes are predicated on a predetermined causality rating between the identified phenotypes and the predictive outcomes.

63. The system of claim 50 wherein the processor is further configured for pre-processing image data including performing one or more of: (i) intensity vector analysis, (ii) image registration and transformation analysis or (iii) anatomic region analysis.

64. The system of claim 50 wherein the imaging features are derived based on one or more of: (i) temporal operators, (ii) fractal analysis, (iii) spatial operators or (iv) or an augmented Markov analysis.

65. The system of claim 50 wherein the logical parameters include one or more of (i) size and/or structure, (ii) composition, (iii) hemodynamics, or (iii) gene expression correlates.

66. The system of claim 50 wherein the imaged target is a lesion and wherein the one or more logical characteristics include (i) a size of the lesion, (ii) a shape of the lesion, (iii) a characterization of the margin of the lesion, (iv) a solidity of the lesion, (v) a heterogeneity of the lesion, (vi) a measure of the lesion's invasive extent or potential extent, (vii) a measure of calcification related to the lesion and (viii) a measure of cell metabolism with respect to the lesion.

67. The system of claim 50 wherein quantification of the one or more logical characteristics includes assessing differences between a plurality of targets.

68. The system of claim 50 wherein the imaged target is a blood vessel and wherein the one or more logical characteristics include (i) an indication of plaque coverage of the vessel wall, (ii) an indication of stenosis of the vessel wall, (iii) an indication of dilation of the vessel wall, and (iv) an indication of vessel wall thickness.

69. The system of claim 50 wherein the imaged target is a vascular tissue and wherein the one or more logical characteristics include (i) an indication of a lipid core of the vascular or related tissue, (ii) a measure of fibrosis of the vascular or related tissue, (iii) a measure of calcification of the vascular or related tissue, (iv) an indication of any hemorrhage in the vascular or related tissue, (v) a measure of permeability of the vascular or related tissue, (vi) an indication of thrombosis of the vascular or related tissue, and (vii) an indication of ulceration of the vascular or related tissue.

70. A processor enabled method comprising:

identifying a set of empirical parameters, the set of empirical parameters including one or more imaging features of the imaged target;

utilizing a first machine learned algorithm to identify and quantify one or more logical characteristics indicated by the empirical parameters, the logical characteristics representing pathological features;

identifying a set of pathological features, the set of pathological features including the one or more quantified logical characteristics; and utilizing a second machine learned algorithm independent from the first machine learned algorithm to identify one or more pathologies indicated by the set of pathological features, wherein the one or more pathologies are indicative of therapeutic/treatment options or further diagnostics;

wherein the first and second algorithms are independently derived utilizing machine learning; and wherein the first algorithm is distinctly trained from the second algorithm.

* * * * *

UNITED STATES PATENT AND TRADEMARK OFFICE

CERTIFICATE OF CORRECTION

PATENT NO. : 10,176,408 B2
APPLICATION NO. : 14/959732
DATED : January 8, 2019
INVENTOR(S) : David S. Paik et al.

It is certified that error appears in the above-identified patent and that said Letters Patent is hereby corrected as shown below:

In the Specification

In Column 1, Line 22, insert the following:
--GOVERNMENT RIGHTS IN THE INVENTION
This invention was in part made with government support under National Science Foundation SBIR Award 1248316 awarded by the National Science Foundation and National Institute of Health SBIR Award R44 HL126224 awarded by the National Institute of Health. The government may have certain rights in the invention.--

Signed and Sealed this
Twenty-fourth Day of January, 2023

Katherine Kelly Vidal

Katherine Kelly Vidal
*Director of the United States Patent and Trademark Office*